US008515506B2

United States Patent
Ridder et al.

(10) Patent No.: US 8,515,506 B2
(45) Date of Patent: Aug. 20, 2013

(54) METHODS FOR NONINVASIVE DETERMINATION OF IN VIVO ALCOHOL CONCENTRATION USING RAMAN SPECTROSCOPY

(75) Inventors: Trent D Ridder, Tucson, AZ (US); Rob Johnson, Federal Way, WA (US); Russell Abbink, Sandia Park, NM (US); John D Maynard, Albuquerque, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 1509 days.

(21) Appl. No.: 12/107,765

(22) Filed: Apr. 23, 2008

(65) Prior Publication Data

US 2009/0234204 A1 Sep. 17, 2009

Related U.S. Application Data

(63) Continuation-in-part of application No. 10/852,415, filed on May 24, 2004, now Pat. No. 7,403,804, which is a continuation-in-part of application No. 10/281,576, filed on Oct. 28, 2002, now Pat. No. 7,202,091, which is a continuation-in-part of application No. 09/832,608, filed on Apr. 11, 2001, now Pat. No. 6,983,176, said application No. 10/852,415 is a continuation-in-part of application No. 10/378,237, filed on Mar. 3, 2003, now Pat. No. 6,865,408, which is a continuation-in-part of application No. 09/832,585, filed on Apr. 11, 2001, now Pat. No. 6,574,490, and a continuation-in-part of application No. 10/281,576, filed on Oct. 28, 2002, now Pat. No. 7,202,091, said application No. 10/852,415 is a continuation-in-part of application No. 10/753,503, filed on Jan. 8, 2004, now Pat. No. 7,016,713.

(51) Int. Cl.
*A61B 5/1455* (2006.01)
*G06F 7/04* (2006.01)
*G05B 19/00* (2006.01)

(52) U.S. Cl.
USPC .......................................... 600/310; 340/5.82

(58) Field of Classification Search
USPC .......................... 600/310, 316, 322; 340/5.82
See application file for complete search history.

(56) References Cited

U.S. PATENT DOCUMENTS

| | | |
|---|---|---|
| 4,592,443 A | 6/1986 | Simon |
| 4,699,149 A | 10/1987 | Rice |

(Continued)

OTHER PUBLICATIONS

Miller et. al. in "Minimally invasive spectroscopic system for intraocular drug detection", Journal of Biomedical Optics 7(1), 27-33 (2002).

(Continued)

*Primary Examiner* — Eric Winakur
(74) *Attorney, Agent, or Firm* — V. Gerald Grafe

(57) ABSTRACT

Methods and apparatuses for the determination of an attribute of the tissue of an individual use non-invasive Raman spectroscopy. For example, the alcohol concentration in the blood or tissue of an individual can be determined non-invasively. A portion of the tissue is illuminated with light, the light propagates into the tissue where it is Raman scattered within the tissue. The Raman scattered light is then detected and can be combined with a model relating Raman spectra to alcohol concentration in order to determine the alcohol concentration in the blood or tissue of the individual. Correction techniques can be used to reduce determination errors due to detection of light other than that from Raman scattering from the alcohol in the tissue. Other biologic information can be used in combination with the Raman spectral properties to aid in the determination of alcohol concentration, for example age of the individual, height of the individual, weight of the individual, medical history of the individual and his/her family, ethnicity, skin melanin content, or a combination thereof. The method and apparatus can be highly optimized to provide reproducible and, preferably, uniform radiance of the tissue, low tissue sampling error, depth targeting of the tissue layers or sample locations that contain the attribute of interest, efficient collection of Raman spectra from the tissue, high optical throughput, high photometric accuracy, large dynamic range, excellent thermal stability, effective calibration maintenance, effective calibration transfer, built-in quality control, and ease-of-use.

25 Claims, 19 Drawing Sheets

(56) References Cited

U.S. PATENT DOCUMENTS

| | | | |
|---|---|---|---|
| 4,703,474 A | 10/1987 | Foschini et al. | |
| 4,738,333 A | 4/1988 | Collier | |
| 4,975,581 A | 12/1990 | Robinson et al. | |
| 4,996,161 A | 2/1991 | Conners | |
| 5,055,268 A | 10/1991 | Martin | |
| 5,224,566 A | 7/1993 | Stepanian | |
| 5,348,002 A | 9/1994 | Caro | |
| 5,348,003 A | 9/1994 | Caro | |
| 5,377,003 A | 12/1994 | Lewis | |
| 5,426,415 A | 6/1995 | Prachar | |
| 5,442,438 A | 8/1995 | Batchelder | |
| 5,553,616 A * | 9/1996 | Ham et al. | 600/316 |
| 5,638,816 A | 6/1997 | Kiani-Azarbayjany | |
| 5,655,530 A | 8/1997 | Messerschmidt | |
| 5,696,582 A | 12/1997 | Barwald | |
| 5,697,373 A | 12/1997 | Richards-Kortum | |
| 5,743,262 A | 4/1998 | Lepper et al. | |
| 5,743,349 A | 4/1998 | Steinberg | |
| 5,747,806 A | 5/1998 | Khalil | |
| 5,751,415 A | 5/1998 | Smith | |
| 5,823,951 A | 10/1998 | Messerschmidt | |
| 5,830,112 A | 11/1998 | Wang et al. | |
| 5,830,132 A | 11/1998 | Robinson et al. | |
| 5,835,213 A | 11/1998 | Curbelo | |
| 5,860,919 A | 1/1999 | Kiani-Azarbayjany | |
| 5,907,407 A | 5/1999 | Atkinson | |
| 5,914,780 A | 6/1999 | Turner et al. | |
| 5,923,422 A | 7/1999 | Keens et al. | |
| 5,945,676 A | 8/1999 | Khalil | |
| 5,953,477 A | 9/1999 | Wach | |
| 5,963,322 A | 10/1999 | Rapp et al. | |
| 6,006,001 A | 12/1999 | Alfano et al. | |
| 6,040,194 A | 3/2000 | Chick | |
| 6,040,578 A | 3/2000 | Malin | |
| 6,067,167 A | 5/2000 | Atkinson | |
| 6,070,093 A * | 5/2000 | Oosta et al. | 600/316 |
| 6,110,522 A | 8/2000 | Lepper et al. | |
| 6,151,516 A | 11/2000 | Kiani-Azarbayjany | |
| 6,152,876 A | 11/2000 | Robinson | |
| 6,157,041 A | 12/2000 | Thomas et al. | |
| 6,219,565 B1 | 4/2001 | Cupp et al. | |
| 6,223,063 B1 | 4/2001 | Chaiken | |
| 6,229,908 B1 | 5/2001 | Edmonds | |
| 6,278,889 B1 | 8/2001 | Robinson | |
| 6,411,373 B1 | 6/2002 | Garside et al. | |
| 6,415,167 B1 | 7/2002 | Blank | |
| 6,424,848 B1 | 7/2002 | Berman | |
| 6,441,388 B1 | 8/2002 | Thomas | |
| 6,493,566 B1 | 12/2002 | Ruchti | |
| 6,512,937 B2 | 1/2003 | Blank | |
| 6,528,809 B1 | 3/2003 | Thomas | |
| 6,559,947 B1 | 5/2003 | Turner | |
| 6,560,352 B2 | 5/2003 | Rowe | |
| 6,574,490 B2 | 6/2003 | Abbink et al. | |
| 6,574,501 B2 | 6/2003 | Lambert | |
| 6,587,196 B1 | 7/2003 | Stippick | |
| 6,587,199 B1 | 7/2003 | Luu | |
| 6,593,101 B2 | 7/2003 | Richards-Kortum | |
| 6,622,032 B1 | 9/2003 | Robinson et al. | |
| 6,628,809 B1 | 9/2003 | Rowe | |
| 6,640,117 B2 | 10/2003 | Makarewicz | |
| 6,654,125 B2 | 11/2003 | Maynard | |
| 6,654,620 B2 | 11/2003 | Wu | |
| 6,678,541 B1 | 1/2004 | Durkin et al. | |
| 6,684,099 B2 | 1/2004 | Ridder et al. | |
| 6,687,521 B2 | 2/2004 | Sato | |
| 6,697,666 B1 | 2/2004 | Richards-Kortum | |
| 6,748,301 B1 | 6/2004 | Ryu | |
| 6,748,792 B1 | 6/2004 | Freund | |
| 6,762,835 B2 | 7/2004 | Zhang | |
| 6,816,241 B2 | 11/2004 | Grubisic | |
| 6,816,605 B2 | 11/2004 | Rowe | |
| 6,862,091 B2 | 3/2005 | Johnson | |
| 6,864,978 B1 | 3/2005 | Hazen | |
| 6,865,408 B1 | 3/2005 | Abbink et al. | |
| 6,870,620 B2 | 3/2005 | Faupel et al. | |
| 6,898,451 B2 | 5/2005 | Wuori | |
| 6,931,268 B1 | 8/2005 | Kiani-Azarbayjany | |
| 6,956,484 B2 | 10/2005 | Crespo | |
| 6,956,649 B2 | 10/2005 | Acosta | |
| 6,961,599 B2 * | 11/2005 | Lambert et al. | 600/318 |
| 6,983,176 B2 | 1/2006 | Gardner | |
| 7,016,713 B2 | 3/2006 | Gardner | |
| 7,038,774 B2 | 5/2006 | Hazen | |
| 7,043,288 B2 | 5/2006 | Davis, III et al. | |
| 7,092,832 B2 | 8/2006 | Brown | |
| 7,098,037 B2 | 8/2006 | Haas | |
| 7,133,710 B2 | 11/2006 | Acosta | |
| 7,136,076 B2 | 11/2006 | Marbach | |
| 7,136,710 B1 | 11/2006 | Hoffberg | |
| 7,147,153 B2 | 12/2006 | Rowe | |
| 7,167,735 B2 * | 1/2007 | Uchida et al. | 600/310 |
| 7,183,102 B2 | 2/2007 | Monfre | |
| 7,194,369 B2 | 3/2007 | Lundstedt | |
| 7,202,091 B2 | 4/2007 | Jones | |
| 7,203,345 B2 | 4/2007 | Rowe | |
| 7,206,623 B2 | 4/2007 | Blank | |
| 7,233,816 B2 | 6/2007 | Blank | |
| 7,263,213 B2 | 8/2007 | Rowe | |
| 7,299,080 B2 | 11/2007 | Acosta | |
| 7,333,843 B2 | 2/2008 | Monfre | |
| 7,347,365 B2 | 3/2008 | Rowe | |
| 7,386,152 B2 | 6/2008 | Rowe | |
| 7,398,119 B2 | 7/2008 | Lambert | |
| 7,403,804 B2 | 7/2008 | Ridder et al. | |
| 7,460,696 B2 | 12/2008 | Rowe | |
| 7,505,801 B2 | 3/2009 | Monfre | |
| 7,508,965 B2 | 3/2009 | Rowe | |
| 7,509,153 B2 | 3/2009 | Blank | |
| 7,519,406 B2 | 4/2009 | Blank | |
| 7,539,330 B2 | 5/2009 | Rowe | |
| 7,545,963 B2 | 6/2009 | Rowe | |
| 7,606,608 B2 | 10/2009 | Blank | |
| 7,613,504 B2 | 11/2009 | Rowe | |
| 7,616,123 B2 | 11/2009 | Ridder et al. | |
| 7,620,212 B1 | 11/2009 | Allen | |
| 7,627,151 B2 | 12/2009 | Rowe | |
| 7,756,558 B2 | 7/2010 | Ridder et al. | |
| 7,848,605 B2 | 12/2010 | Ridder et al. | |
| 7,889,349 B2 | 2/2011 | Ridder et al. | |
| 2003/0032064 A1 | 2/2003 | Soller | |
| 2003/0163710 A1 | 8/2003 | Ortiz | |
| 2004/0204868 A1 | 10/2004 | Maynard | |
| 2005/0130321 A1 | 6/2005 | Nicholson | |
| 2005/0230175 A1 | 10/2005 | Brown | |
| 2005/0261560 A1 | 11/2005 | Ridder et al. | |
| 2006/0002597 A1 | 1/2006 | Rowe | |
| 2006/0002598 A1 | 1/2006 | Rowe | |
| 2006/0062438 A1 | 3/2006 | Rowe | |
| 2006/0110015 A1 | 5/2006 | Rowe | |
| 2006/0167349 A1 | 7/2006 | Gardner | |
| 2006/0173256 A1 | 8/2006 | Ridder et al. | |
| 2006/0202028 A1 | 9/2006 | Rowe | |
| 2006/0210120 A1 | 9/2006 | Rowe | |
| 2006/0244947 A1 | 11/2006 | Rowe | |
| 2006/0274921 A1 | 12/2006 | Rowe | |
| 2007/0030475 A1 | 2/2007 | Rowe | |
| 2007/0731888 | 3/2007 | Ridder et al. | |
| 2007/0142720 A1 | 6/2007 | Ridder et al. | |
| 2007/0230754 A1 | 10/2007 | Jain | |
| 2007/0239992 A1 | 10/2007 | White | |
| 2008/0025579 A1 | 1/2008 | Sidlauskas | |
| 2008/0025580 A1 | 1/2008 | Sidlauskas | |
| 2008/0192988 A1 | 8/2008 | Uludag | |
| 2008/0208018 A1 | 8/2008 | Ridder et al. | |
| 2008/0232653 A1 | 9/2008 | Rowe | |
| 2008/0297788 A1 | 12/2008 | Rowe | |
| 2008/0298649 A1 | 12/2008 | Ennis | |

| | | |
|---|---|---|
| 2008/0304712 A1 | 12/2008 | Rowe |
| 2008/0319286 A1 | 12/2008 | Ridder et al. |
| 2009/0046903 A1 | 2/2009 | Corcoran |
| 2009/0074255 A1 | 3/2009 | Holm |
| 2009/0080709 A1 | 3/2009 | Rowe |
| 2009/0092290 A1 | 4/2009 | Rowe |
| 2009/0148005 A1 | 6/2009 | Rowe |
| 2009/0234204 A1 | 9/2009 | Ridder et al. |
| 2009/0245591 A1 | 10/2009 | Rowe |
| 2009/0247840 A1 | 10/2009 | Blank |
| 2010/0010325 A1 | 1/2010 | Ridder et al. |
| 2011/0178420 A1 | 7/2011 | Ridder et al. |
| 2012/0078473 A1 | 3/2012 | Ridder et al. |

OTHER PUBLICATIONS

Brault, "New Approach to High-Precision Fourier Transform Spectrometer Design," Applied Optics, vol. 35, No. 16, Jun. 1, 1996, pp. 2891-2896.

Brasunas and Cusman, "Uniform Time-Sampling Fourier Transform Spectroscopy," Applied Optics, vol. 36, No. 10, Apr. 1, 1997, pp. 2206-2210.

* cited by examiner

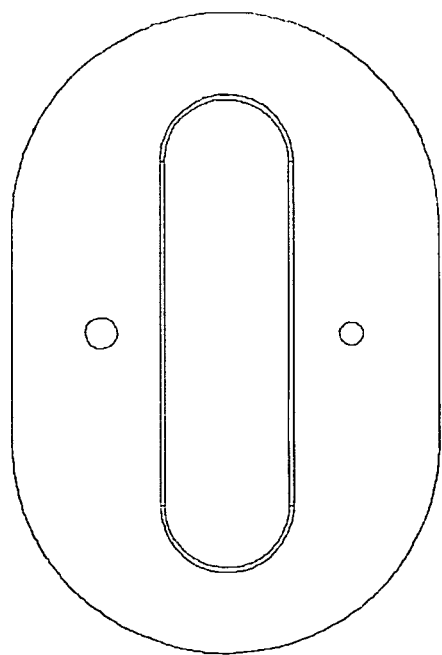
Fig. 10

METHODS FOR NONINVASIVE DETERMINATION OF IN VIVO ALCOHOL CONCENTRATION USING RAMAN SPECTROSCOPY

CROSS REFERENCES TO CO-PENDING APPLICATIONS

This application is a continuation-in-part of U.S. patent application Ser. No. 10/852,415, "Noninvasive Determination of Alcohol in Tissue", filed May 24, 2004, which application (a) is a continuation-in-part of U.S. patent application Ser. No. 10/281,576, entitled "Optically Similar Reference Samples", filed Oct. 28, 2002, now U.S. Pat. No. 7,202,091 issued Apr. 10, 2007, incorporated herein by reference, which is a continuation-in-part of U.S. patent application Ser. No. 09/832,608, entitled "Optically Similar Reference Samples and Related Methods for Multivariate Calibration Models Used in Optical Spectroscopy," filed Apr. 11, 2001, now U.S. Pat. No. 6,983,176 issued Jan. 3, 2006; and (b) is a continuation-in-part of U.S. patent application Ser. No. 10/378,237, entitled "System For Non-Invasive Measurement Of Glucose In Humans," filed Mar. 3, 2003, now U.S. Pat. No. 6,865,408 issued Mar. 8, 2005, incorporated herein by reference, which is (b1) a continuation-in-part of U.S. patent application Ser. No. 09/832,585, entitled "System For Non-Invasive Measurement Of Glucose In Humans," filed Apr. 11, 2001, now U.S. Pat. No. 6,574,490 issued Jun. 3, 2003, incorporated herein by reference; and (b2) a continuation-in-part of U.S. patent application Ser. No. 10/281,576, entitled "Optically Similar Reference Samples", filed Oct. 28, 2002, now U.S. Pat. No. 7,202,091 issued Apr. 10, 2007; and (c) is a continuation-in-part of U.S. patent application Ser. No. 10/753,506, "Noninvasive Determination of Direction and Rate of Change of an Analyte," filed Jan. 8, 2004, now U.S. Pat. No. 7,016,713 issued Mar. 21, 2006, incorporated herein by reference.

FIELD OF THE INVENTION

The present invention generally relates to determination of alcohol concentration in humans using Raman spectroscopy. More specifically, the present invention relates to methods and apparatuses for determining alcohol concentrations using Raman spectra, and for determining properties of Raman spectra in tissue, and for determination of identity from Raman spectral properties and from appropriate models.

BACKGROUND OF THE INVENTION

Current practice for alcohol measurements is based upon either blood measurements or breath testing. Blood measurements define the gold standard for determining alcohol intoxication levels. However, blood measurements require either a venous or capillary sample and involve significant handling precautions in order to minimize health risks. Once extracted, the blood sample must be properly labeled and transported to a clinical laboratory or other suitable location where a clinical gas chromatograph is typically used to measure the blood alcohol level. Due to the invasiveness of the procedure and the amount of sample handling involved, blood alcohol measurements are usually limited to critical situations such as for traffic accidents, violations where the suspect requests this type of test, and accidents where injuries are involved.

Because it is less invasive, breath testing is more commonly encountered in the field. In breath testing, the subject must expel air into the instrument for a sufficient time and volume to achieve a stable breath flow that originates from the alveoli deep within the lungs. The device then measures the alcohol content in the air, which is related to blood alcohol through a breath-blood partition coefficient. The blood-breath partition coefficient used in the United States is 2100 (implied units of mg EtOH/dL blood per mg EtOH/dL air) and varies between 1900 and 2400 in other nations. The variability in the partition coefficient is due to the fact that it is highly subject dependent. In other words, each subject will have a partition coefficient in the 1900 to 2400 range that depends on his or her physiology. Since knowledge of each subject's partition coefficient is unavailable in field applications, each nation assumes a single partition coefficient value that is globally applied to all measurements. In the U.S., defendants in DUI cases often use the globally applied partition coefficient as an argument to impede prosecution.

Breath measurements have additional limitations. First, the presence of "mouth alcohol" can falsely elevate the breath alcohol measurement. This necessitates a 15-minute waiting period prior to making a measurement in order to ensure that no mouth alcohol is present. For a similar reason, a 15 minute delay is required for individuals who are observed to burp or vomit. A delay of 10 minutes or more is often required between breath measurements to allow the instrument to return to equilibrium with the ambient air and zero alcohol levels. In addition, the accuracy of breath alcohol measurements is sensitive to numerous physiological and environmental factors.

Multiple government agencies, and society in general, seek non-invasive alternatives to blood and breath alcohol measurements. Quantitative spectroscopy offers the potential for a completely non-invasive alcohol measurement that is not sensitive to the limitations of the current measurement methodologies. While non-invasive determination of biological attributes by quantitative spectroscopy has been found to be highly desirable, it has been very difficult to accomplish. Attributes of interest include, as examples, analyte presence, analyte concentration (e.g., alcohol concentration), direction of change of an analyte concentration, rate of change of an analyte concentration, disease presence (e.g., alcoholism), disease state, and combinations and subsets thereof. Non-invasive measurements via quantitative spectroscopy are desirable because they are painless, do not require a fluid draw from the body, carry little risk of contamination or infection, do not generate any hazardous waste, and can have short measurement times.

Several approaches have been proposed for the non-invasive determination of attributes of biological tissue. These systems have included technologies incorporating polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photo-acoustic spectroscopy, and near-infrared spectroscopy. However, these systems have not replaced existing approaches for the measurement of alcohol concentration.

U.S. Patent application 20050090750 (Ediger) discloses the use of Raman spectroscopy of tissue to screen for diabetes. It does not disclose the use of Raman spectroscopy for the measurement of alcohol concentration or application as a biometric method.

U.S. Pat. No. 5,553,616 (Ham) discloses instruments and methods for noninvasive tissue glucose level monitoring via Raman spectroscopy and spectral processing by neural networks and fuzzy logic. Ham does not describe measurement of any other tissue property such as alcohol, or any method of screening for alcohol, or determining biometric identity.

U.S. Pat. No. 5,582,168 (Samuels) discloses apparatus and methods for measuring characteristics of biological tissues and similar materials. These apparatus and methods are described with respect to measurements of the human eye. In addition, the correction methodologies described by these inventors involve only measurements of the elastically scattered excitation light. Samuels describes a simple linear correction technique. Samuels does not disclose noninvasive measurements that allow determination of alcohol concentration or biometric measurements.

U.S. Pat. No. 5,882,301 (Yoshida) discloses methods and apparatus for obtaining Raman emission from intraocular substances including advanced glycated endproducts (AGEs). Yoshida does not disclose noninvasive measurements that allow determination of alcohol concentration or biometric measurements.

U.S. Pat. No. 6,044,285 (Chaiken) discloses a system based upon Raman spectroscopy for measuring blood glucose. The described technique relies upon an absorbing species such as hemoglobin acting as a temperature probe. Chaiken does not disclose noninvasive measurements that allow determination of alcohol concentration or biometric measurements. In addition, Chaiken does not describe methods for correction techniques to compensate for local skin absorption or scattering.

U.S. Pat. No. 6,167,290 (Yang) discloses a Raman spectroscopy system for noninvasively measuring blood glucose. Yang does not disclose noninvasive measurements that allow determination of alcohol concentration or biometric measurements. Furthermore, Yang does not describe methods for correction techniques to compensate for local skin absorption or scattering in order to recover the intrinsic Raman emission signal.

U.S. Pat. No. 6,289,230 (Chaiken) describes an apparatus for the non-invasive quantification of glucose via Raman spectroscopy. Chaiken does not disclose noninvasive measurements that allow determination of alcohol concentration or biometric measurements. In addition, Chaiken does not describe methods for correction techniques to compensate for local skin absorption or scattering.

U.S. Pat. No. 6,352,502 (Chaiken) describes an apparatus based upon Raman spectroscopy for the noninvasive characterization of skin and detection of skin abnormalities. Chaiken does not disclose noninvasive measurements that allow determination of alcohol concentration or biometric measurements. Chaiken does not describe methods to extract the intrinsic Raman emission from the detected signal nor multivariate techniques to quantitatively predict analyte concentration.

U.S. Pat. Nos. 6,181,957 and 6,424,850 (Lambert) describe a noninvasive glucose monitor that uses Raman spectroscopy. The inventions require interrogation of the anterior chamber of the eye. Furthermore, other than Fluorescence subtraction, Lambert does not disclose algorithms or methods for recovering intrinsic Raman emission or other techniques to compensate for local tissue variations.

U.S. Pat. No. 6,560,478 (Alfano) describes an apparatus based upon Raman spectroscopy for examining biological materials. Alfano discloses that the technique can be applied for the diagnosis of disease by measuring characteristic Raman emission associated with blood glucose and other constituents. Alfano does not disclose noninvasive measurements that allow determination of alcohol concentration or biometric measurements. Also, Alfano does not disclose algorithms or methods for recovering intrinsic Raman emission or other techniques to compensate for local tissue variations.

U.S. Pat. No. 7,257,987 and applications 20070271997 and 20060144126 (O'Brien) disclose apparatuses for measuring analytes in gases including alcohol in breath. The present invention involves in vivo, rather than ex vivo, alcohol measurements and therefore does not involve the use of breath. Furthermore, none of the O'Brien patents or applications disclose algorithms or methods for recovering intrinsic Raman emission or other techniques to compensate for local tissue variations.

U.S. Patent application 20070239992 (White) discloses the use of spectroscopic alcohol measurements as part of an automotive interlock. White does not disclose any embodiments of Raman systems for alcohol measurements nor does White disclose algorithms or methods for recovering intrinsic Raman emission or other techniques to compensate for local tissue variations.

U.S. Pat. No. 6,070,093 (Oosta) discloses the use of multiplex sensors that combine multiple measurement modalities (e.g. absorbance combined with Raman) to measure analytes. The present invention does not require the combination of multiple modalities. Furthermore, Oosta does not disclose embodiments of suitable Raman systems for alcohol measurements nor does Oosta disclose algorithms or methods for recovering intrinsic Raman emission or other techniques to compensate for local tissue variations.

A research group at Duke University (Brady) has disclosed embodiments of multimodal multiplex Raman spectroscopy for measuring alcohol. Multimodal Multiplex Raman uses multiple excitation lasers within a single instrument, each having a different lasing wavelength. Raman spectra are then collected from a sample using each laser. Additional details can be found in "Multimodal multiplex Raman spectroscopy optimized for in vivo chemometrics", Biomedical Vibrational Spectroscopy III: Advances in Research and Industry, Proc. of SPIE Vol. 6093 (2006). The present invention does not require the use of multiple excitation lasers.

Instruments and methods useful in Raman spectroscopy like that in the present invention have been described for other applications. See, e.g., Toshima et al., Jpn J Ophthalmol, 1990; Nie et al., Exp Eye Res, 1990 (evaluation of lens water content, and cataract progression); Sebag et al., Invest Ophthalmol Visual Sci, 1994 (evaluation of the progression of retinopathy); Shim and Wilson, J Raman Spectroscopy, 1996 (characterization of fundamental Raman-active bonds in skin); Caspers et al., Biospectoscopy, 1998 and Caspers et al., J Invest Derm, 2001, (study of natural moisturizing factor in stratum corneum); Caspers et al., Biophysical J, 2002 (Raman confocal microscopy of skin).

SUMMARY OF THE INVENTION

The present invention provides a method of determining the alcohol concentration in the blood or tissue of an individual. A portion of the tissue of the individual is illuminated with light, the light propagates into the tissue where a portion is Raman scattered within the tissue. A portion of the Raman scattered light is then detected and can be combined with a model relating Raman spectra to alcohol concentration in order to determine the alcohol concentration in the blood or tissue of an individual.

The invention can comprise single wavelength excitation light, scanning of excitation light (illuminating the tissue at a plurality of wavelengths), detection at a single or multiple wavelengths, scanning of detection wavelengths (detecting emitted light at a plurality of wavelengths), and combinations thereof. The invention also can comprise correction techniques that reduce determination errors due to detection of light other than that from Raman scattering of a chemical in the tissue. For example, the reflectance of the tissue can lead to errors if appropriate correction is not employed.

The invention can also comprise a variety of models relating Raman spectra to alcohol concentration, including a variety of methods for generating such models. Other biologic information can be used in combination with the Raman spectral properties to aid in the determination of alcohol concentration, for example age of the individual, height of the individual, weight of the individual, medical history of the individual and his/her family, ethnicity, skin melanin content, or a combination thereof. The invention also comprises apparatuses suitable for carrying out the method, including appropriate light sources, detectors, and models (for example, implemented on computers) used to relate detected Raman scattering and alcohol concentration.

The present invention documents a multidisciplinary approach to the design of a spectroscopic instrument that incorporates an understanding of the instrument subsystems, tissue physiology, multivariate analysis, Raman spectroscopy and overall system operation. Further, the interactions between the subsystems have been analyzed so that the behavior and requirements for the entire non-invasive measurement device are well understood and result in a design for a commercial instrument that will make non-invasive measurements with sufficient accuracy and precision at a price and size that is commercially viable.

Embodiments of Raman monitors can be considered in terms of multiple subsystems. The subsystems of the Raman monitors of the present invention are optimized to provide reproducible and uniform radiance of the tissue or sample, low tissue sampling error, depth targeting of the tissue layers or sample locations that contain the property of interest, efficient collection of Raman spectra from the tissue or sample, high optical throughput, high photometric accuracy, large dynamic range, excellent thermal stability, effective calibration maintenance, effective calibration transfer, built-in quality control, and ease-of-use.

BRIEF DESCRIPTION OF THE DRAWINGS

FIG. 10 shows an example ergonomic apparatus located on the measurement site.

FIG. 19 is a visual presentation of the inter-subject resolving power of spectroscopic measurements.

DETAILED DESCRIPTION OF THE INVENTION

Figure 1:
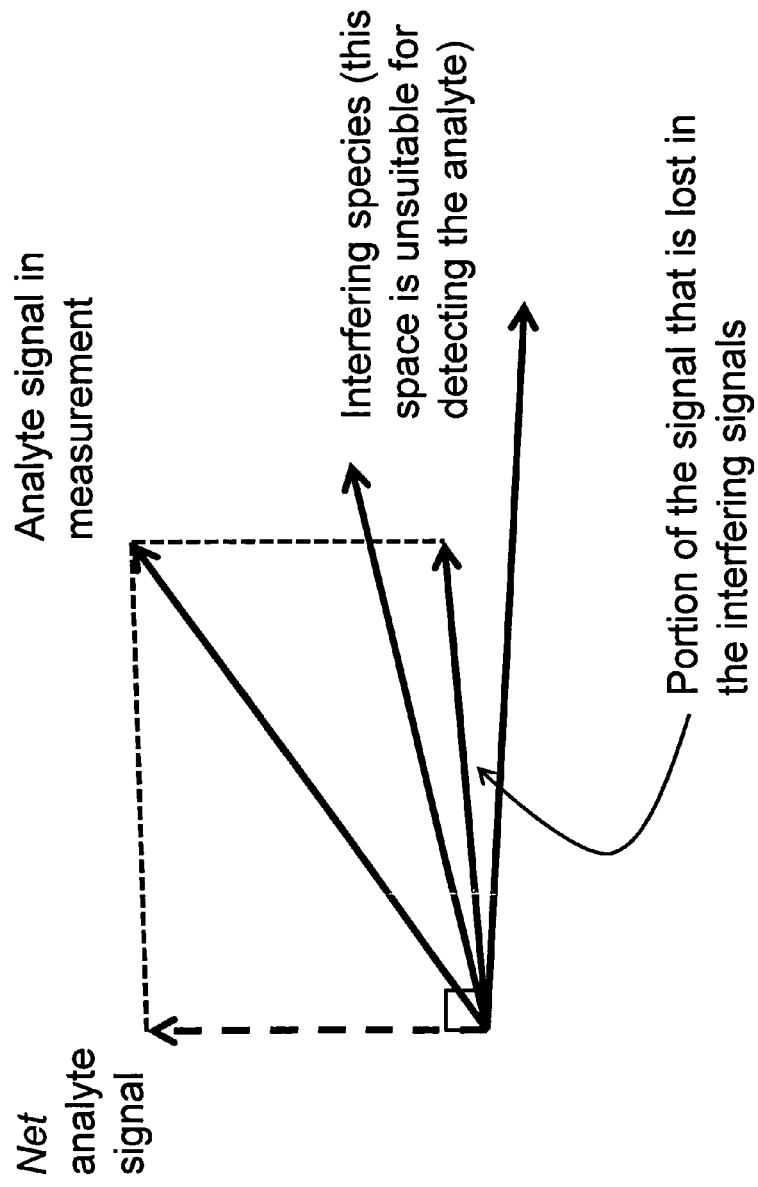
FIG. 1 is a graphical representation of the net attribute signal in a three dimensional system.

"Tissue reflectance characteristic" includes any reflectance property of tissue that is useful in correction of detected light, including as examples the tissue reflectance at the Raman excitation wavelength, the tissue reflectance at the Raman scattering wavelength, and the tissue reflectance at other wavelengths found useful for estimating the tissue's intrinsic Raman scattering spectrum. When light is described as having a "single wavelength," it is understood that the light can actually comprise light at a plurality of wavelengths, but that a significant portion of the energy in the light is transmitted at a single wavelength or at a range of wavelengths near a single wavelength.

For the purposes of this invention, the term "analyte concentration" generally refers to the concentration of an analyte such as alcohol. The term "analyte property" includes analyte concentration and other properties, such as the presence or absence of the analyte or the direction or rate of change of the analyte concentration, which can be measured in conjunction with or instead of the analyte concentration. While the term "analyte" generally refers to alcohol, other chemicals, particularly substances of abuse and alcohol byproducts, can also benefit from the present invention. For the purposes of this invention, the term "alcohol byproducts" includes the adducts, biomarkers, and byproducts of the metabolism of alcohol by the body including, but not limited to, acetone, acetaldehyde, Gamma Glutamyl Transferase (GGT), Aspartate Amino Transferase (AST), Alanine Amino Transferase (AST), Ethyl Glucuronide (EtG), Ethyl Sulphate (EtS), Phosphatidyl Ethanol (PEth), CDT, Mean Corpuscular Volume (MCV), Carbohydtrate Deficient Transferrin (CDT), and acetic acid.

The term "substances of abuse" refers to, but is not limited to, THC (Tetrahydrocannabinol or marijuana), cocaine, M-AMP (methamphetamine), OPI (morphine and heroin), OxyContin, Oxycodone, and PCP (phencyclidine). The present invention addresses this need for analyte measurements of samples utilizing spectroscopy where the term "sample" generally refers to biological tissue. The term "subject" generally refers to a person from whom a sample measurement was acquired.

For the purposes of this invention the term "dispersive spectrometer" indicates a spectrometer based upon any device, component, or group of components that spatially separate one or more wavelengths of light from other wavelengths. Examples include, but are not limited to spectrometers that use one or more ruled diffraction gratings, prisms, holographic gratings, or combinations thereof. For the purposes of this invention the term "interferometric/modulating spectrometer" indicates a class of spectrometers based upon any device, component, or group of components that either modulate different wavelengths of light to different frequencies in time or selectively transmits or reflects certain wavelengths of light based upon the properties of light interference. Examples include, but are not limited to Fourier transform interferometers, Hadamard spectrometers, Sagnac interferometers, mock interferometers, Michelson interferometers, one or more etalons, acousto-optical tunable filters (AOTF's), and one or more LED's or VCSEL's that are scanned or modulated. One skilled in the art recognizes that spectrometers based on combinations of dispersive and interferometric/modulating properties, such as those based on lamellar gratings, are also suitable for the present invention.

The invention makes use of "signals", described in some of the examples as Raman scattering or other spectroscopic measurements. Signals can comprise any measurement obtained concerning the spectroscopic measurement of a sample or change in a sample, e.g., absorbance, reflectance, scattering, intensity of light returned, fluorescence, transmission, Raman spectra, or various combinations of measurements, at one or more wavelengths. Some embodiments make use of one or more "models", where such a model can be anything that relates a signal to the desired property. Some examples of models include those derived from multivariate analysis methods such as partial least squares regression (PLS), linear regression, multiple linear regression (MLR), classical least squares regression (CLS), neural networks, discriminant analysis, principal components analysis (PCA), principal components regression (PCR), cluster analysis, and K-nearest neighbors. Single or multi-wavelength models based on the Beer-Lambert law are special cases of classical least squares and are thus included in the term multivariate analysis for the purposes of the present invention.

For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

The present invention can determine analyte properties, such as alcohol or substance of abuse concentration or biometric signals, in the tissue or blood of a subject using one or more noninvasive Raman measurements. The invention can illuminate a portion of the tissue of the individual (e.g., a portion of the skin) with light and detect Raman scattered light from the tissue. The characteristics of the Raman scattered light convey information about the analyte property (e.g. alcohol concentration) of the tissue or sample under interrogation. The invention can apply additional processing and correction algorithms to the measured Raman spectra before determining the analyte property.

Embodiments of Raman Systems Suitable for Noninvasive Alcohol Measurements

The present system overcomes the challenges posed by the complex nature of tissue by incorporating a design that includes, in some embodiments, five highly optimized subsystems. The design contends with the complexities of the tissue spectrum, high signal-to-noise ratio and photometric accuracy requirements, tissue sampling errors, calibration maintenance problems, calibration transfer problems plus a host of other issues. The five subsystems include an illumination subsystem, a tissue sampling subsystem, a spectrometer subsystem, a computing subsystem, and a calibration subsystem.

The present invention further includes apparatus and methods that allow for implementation and integration of each of these subsystems in order to maximize the net attribute signal-to-noise ratio. The net attribute signal is the portion of the Raman spectrum that is specific for the attribute of interest because it is orthogonal to all other sources of spectral variance. The orthogonal nature of the net attribute signal makes it perpendicular to the space defined by any interfering species and as a result, the net attribute signal is uncorrelated to these sources of variance. The net attribute signal-to-noise ratio is directly related to the accuracy and precision of the present invention for non-invasive determination of the attribute by quantitative Raman spectroscopy. FIG. 1 is a graphical representation of a net attribute signal (e.g., the net analyte signal) in a three dimensional system.

The present invention documents a multidisciplinary approach to the design of a spectroscopic instrument that incorporates an understanding of the instrument subsystems, tissue physiology, multivariate analysis, Raman spectroscopy and overall system operation. Further, the interactions between the subsystems have been analyzed so that the behavior and requirements for the entire non-invasive measurement device are well understood and result in a design for a commercial instrument that will make non-invasive measurements with sufficient accuracy and precision at a price and size that is commercially viable.

The subsystems of the non-invasive monitor are highly optimized to provide reproducible and, preferably, uniform radiance of the tissue, low tissue sampling error, depth targeting of the tissue layers that contain the property of interest, efficient collection of desired light from the tissue, high optical throughput, high photometric accuracy, large dynamic range, excellent thermal stability, effective calibration maintenance, effective calibration transfer, built-in quality control, and ease-of-use.

Figure 2:
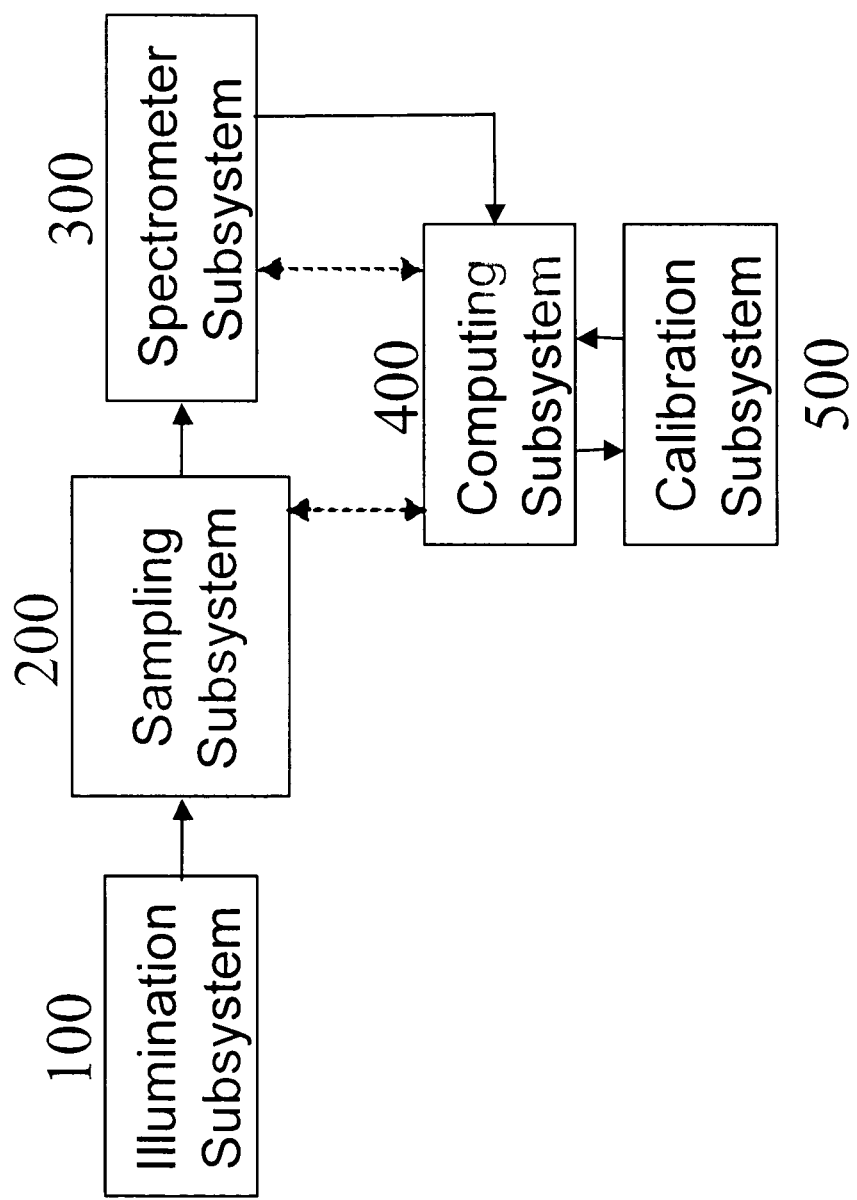
FIG. 2 is a diagrammed view of a Raman measurement system.

Embodiments of a noninvasive Raman monitor can be viewed for discussion purposes as comprising five subsystems; those skilled in the art will appreciate other subdivisions of the functionality disclosed. The subsystems include an illumination subsystem 100, a sampling subsystem 200, a spectrometer subsystem 300, a computing subsystem 400, and a calibration subsystem 500. The subsystems can be designed and integrated in order to achieve a desirable net attribute signal-to-noise ratio. FIG. 2 is a diagrammed view of the entire system. Each of the subsystems is discussed below in detail.

Illumination Subsystem

The illumination subsystem 100 generates the light used to interrogate the tissue, blood, or other sample. The illumination subsystem, in an exemplary embodiment uses a continuous-wave diode laser as the light source. Other examples of suitable light sources include pulsed, modulated or mode-locked lasers as well as solid-state (e.g. VCSEL's), organic light emitting diodes, solid state light emitting diodes, or gas lasers. In some embodiments, broad-band light sources can be combined with line filters in order to achieve a suitably narrow (in wavelength) light source.

In addition to the light source, the illumination subsystem can contain optical elements that collect the radiation from the light source and transfer that light to the input of the tissue sampling subsystem. The elements that makeup the transfer optics can include collimating and/or condensing optics, optical filters, optical diffusers, a reflective integrating chamber, a diffuse integrating chamber, a homogenizer or light pipe for scrambling and the corresponding mechanical components to hold the optics and light source.

In some embodiments, the illumination subsystem can also contain the optical elements that deliver light to the tissue. In these embodiments, the illumination subsystem can be considered a part of the tissue sampling subsystem. In this case, the number of overall optical components can be reduced which can result in a reduced cost, an improvement in optical efficiency, and smaller physical size.

Collimating optics in the illumination subsystem can be refractive or reflective elements. A lens is an example of a refractive collimating optic. A parabolic mirror is an example of a reflective collimating optic. Condensing (e.g. focusing) optics can also be refractive or reflective. A lens is an example of a refractive condensing optic. An elliptical mirror is an example of a reflective condensing optic. Suitable materials for lenses and mirrors are known in the art. The reflective optics can have a smooth finish, a rough finish or a faceted finish depending on the configuration of the illumination subsystem. The rough or faceted finishes for the reflective optics destroy the coherence of the light source image to create a more uniform radiance pattern. The refractive optics can be spherical or aspherical. A Fresnel lens, a special type of aspherical lens, also can be employed. The collimating and/or condensing optics collect radiation from the source and transfer the radiation to the input of the tissue sampling subsystem 200 or to other optical elements that perform additional operations on the light before it is passed to the tissue sampling subsystem 200.

One or more optical filters can be employed to preferentially pass radiation only in the spectral region of interest. The optical filter can be one or a combination of long pass, short pass, or band pass filters. These filters can be absorptive, interference or dichroic in nature. In some embodiments, the optical filters are anti-reflection coated to preserve the transmittance of light in the spectral region of interest. These filters can also perform spectral shaping, such as elimination or suppression of unwanted blackbody radiation or Raman scattering from components within the illumination subsystem. The optical filtering can bandlimit the radiation impinging on the tissue to increase the SNR in the region of interest and to keep from burning or otherwise damaging the tissue of the subject. In embodiments incorporating an interferometric/modulating spectrometer, bandlimiting the radiation can improve the net attribute signal by reducing Shot noise that results from unwanted radiation outside the spectral region of interest.

The optical diffusers and scramblers in the illumination subsystem provide reproducible and, preferably, uniform radiance at the input of the tissue sampling subsystem 200. Uniform radiance can ensure good photometric accuracy and even illumination of the tissue. Uniform radiance can also reduce errors associated with manufacturing differences between light sources. Uniform radiance can be utilized in the present invention for achieving accurate and precise measurements. See, e.g., U.S. Pat. No. 6,684,099, incorporated herein by reference.

A ground glass plate is an example of an optical diffuser. The ground surface of the plate effectively scrambles the angle of the radiation emanating from the light source and its transfer optics. A light pipe can be used to scramble the intensity of the radiation such that the intensity is spatially uniform at the output of the light pipe. In addition, light pipes with a double bend will scramble the angles of the radiation. For creation of uniform spatial intensity and angular distribution, the cross section of the light pipe should not be circular. Square, hexagonal and octagonal cross sections are effective scrambling geometries. The output of the light pipe can directly couple to the input of the tissue sampler or can be used in conjunction with additional transfer optics before the light is sent to the tissue sampler. See, e.g., U.S. patent application Ser. No. 09/832,586, "Illumination Device and Method for Spectroscopic Analysis," incorporated herein by reference.

Sampling Subsystem

Figure 3:
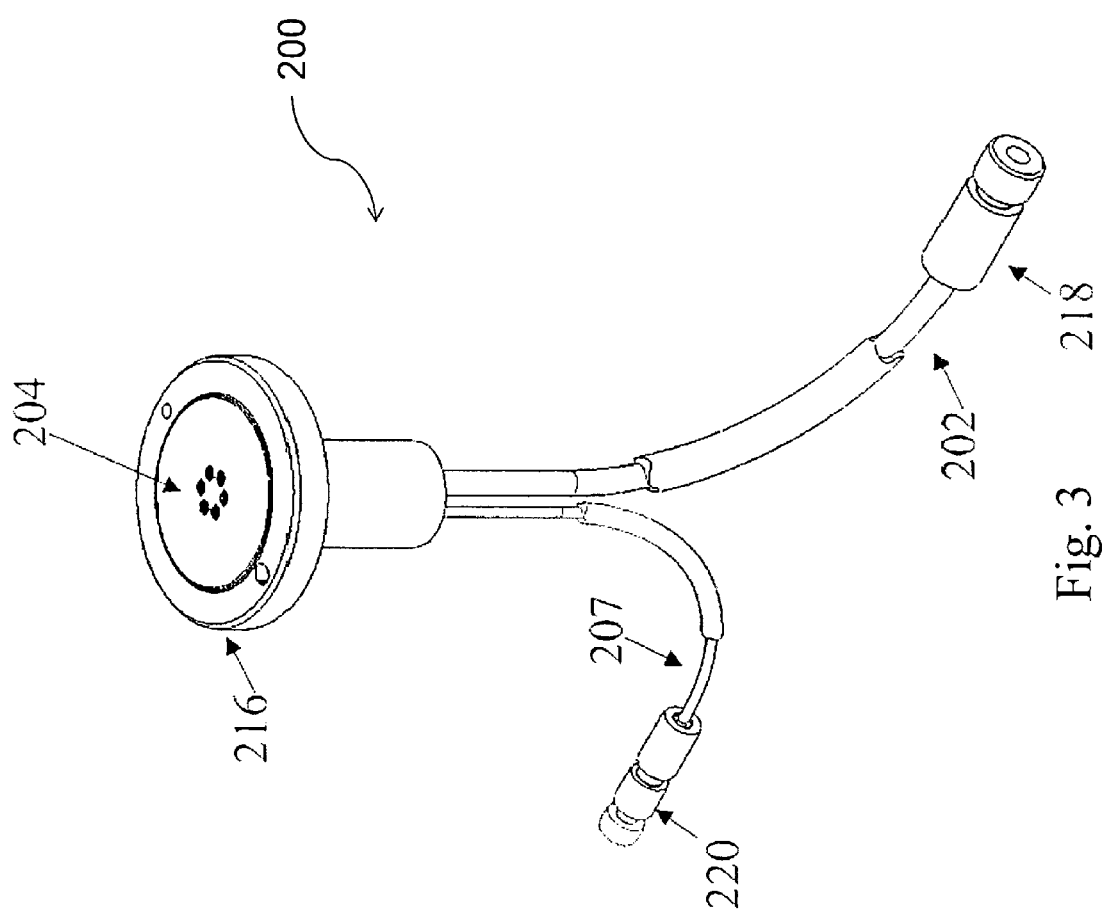
FIG. 3 is a diagrammed view of the sampling subsystem.

The sampling subsystem serves to deliver and collect light from the sample of interest using an optical probe while providing means for promoting good contact and orientation between the sample (e.g. tissue) and the optical probe. Referring to FIG. 3, the tissue sampling subsystem 200 has an optical input 202 (with associated connection device 218) to receive light from the illumination subsystem, a sampling surface 204 which forms a tissue interface 206 that interrogates the tissue and an optical output 207 (with associated connection device 220). The subsystem can further include an ergonomic apparatus (not shown) that holds the sampling surface 204 and positions the tissue at the interface 216. The optical configuration of the sampling surface 204 can take many forms, an overview of which is presented below.

Embodiments of the Optical Probe

Optical fibers are a common material used in the fabrication of optical probes as they allow efficient transfer of light from the illumination subsystem to the sample and from the sample to the spectrometer subsystem. Thus, the optical probe can be considered in two halves; illumination and collection. Some embodiments of the optical probe of the present invention use distinct illumination and collection fibers, thereby allowing many different optical probe geometries. Furthermore, separate illumination and collection fibers also allows a line filter to be placed between the illumination fibers and the sample in order to filter out Raman scattered light arising from the illumination subsystem and/or the illumination fibers of the optical probe. The line filter can also be effective at removing any broad-band emission from the light source in the illumination subsystem as well as unwanted blackbody emission from optical components and surfaces. In other words, the line filter only passes the narrow bandwidth of the laser in the illumination subsystem. A high pass filter can be incorporated between the sampling interface and spectrometer subsystem in order to attenuate or block Rayleigh scattered light from reaching the detector.

Figure 4:
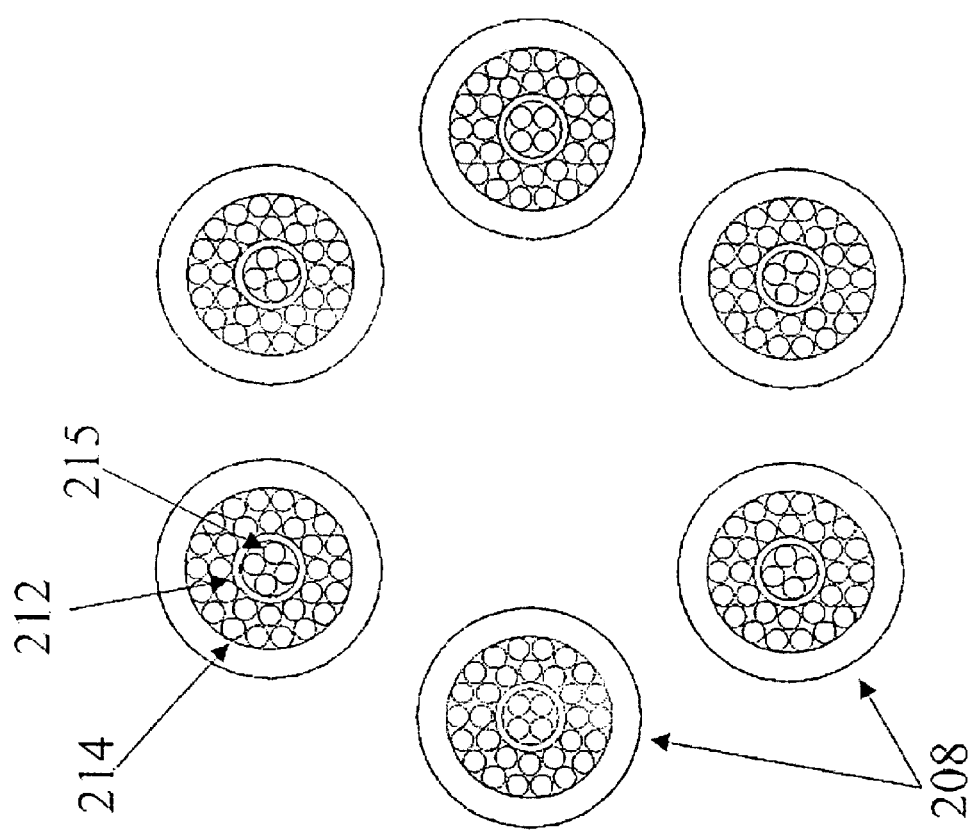
FIG. 4 is depicts an example embodiment of an optical probe.

As an example, the optical input 207 can comprise a bundle of optical fibers that are arranged in a geometric pattern that collects an appropriate amount of light from the illumination subsystem 100. FIG. 4 depicts one example arrangement. The plan view depicts the ends of the input and output fibers in a geometry at the sampling surface including six clusters 208 arranged in a circular pattern. Each cluster includes four central output fibers 215 which collect light from the tissue. Around each grouping of four central output fibers 215 is a cylinder of material 212 which ensures about a 100 μm gap between the edges of the central output fibers 215 and the inner ring of input fibers 214. The 100 μm gap can be important to measuring analytes such as alcohol in the dermis. As shown in FIG. 4, two concentric rings of input fibers 214 are arranged around the cylinder of material 212. As shown in one example embodiment, 32 input fibers surround four output fibers.

Figure 5:
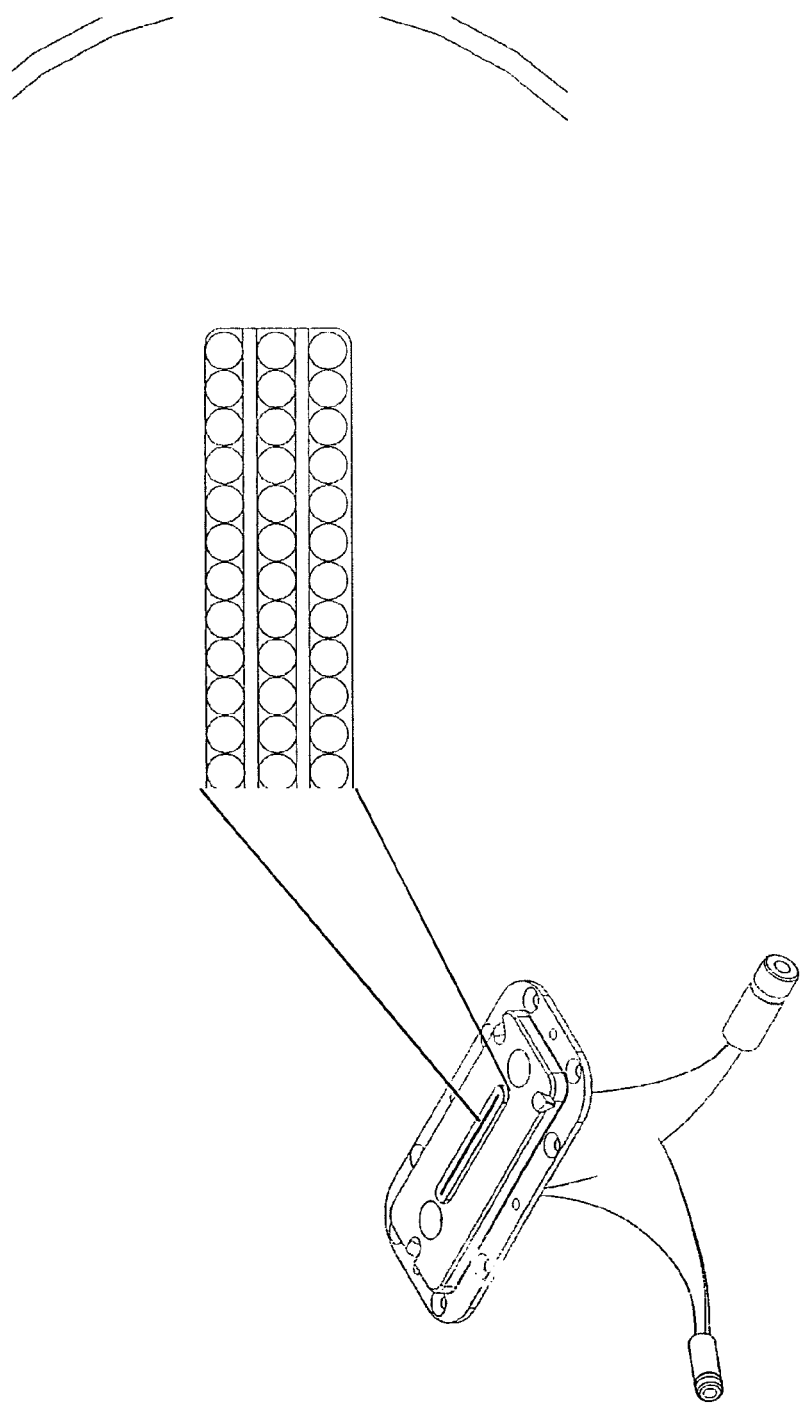
FIG. 5 is depicts an example embodiment of an optical probe.

FIG. 5 demonstrates an alternative to cluster geometries for the sampling subsystem. In this embodiment, the illumination and collection fiber optics are arranged in a linear geometry. Each row can be either for illumination or light collection and can be of any length suitable to achieve sufficient signal to noise. In addition, the number of rows can be 2 or more in order to alter the physical area covered by the sampling subsystem. The total number of potential illumination fibers can depend on the physical size of emissive area of the light source and the diameter of each fiber. Multiple light sources can be used to increase the number of illumination fibers. Furthermore, single-mode, rather than multi-mode fibers can be suitable for the illumination of the same in some embodiments. The number of collection fibers depends upon the area of the interface to the interferometer subsystem. If the number of collection fibers results in an area larger than the interferometer subsystem interface allows, a light pipe or other homogenizer followed by an aperture can be used to reduce the size of the output area of the sampling subsystem. The purpose of the light pipe or other homogenizer is to ensure that each collection fiber contributes equally to the light that passes through the aperture. The illumination light can also be collimated, diverging, or focused depending on the specific embodiment in order to control the propagation of the light through the tissue.

Figure 6:
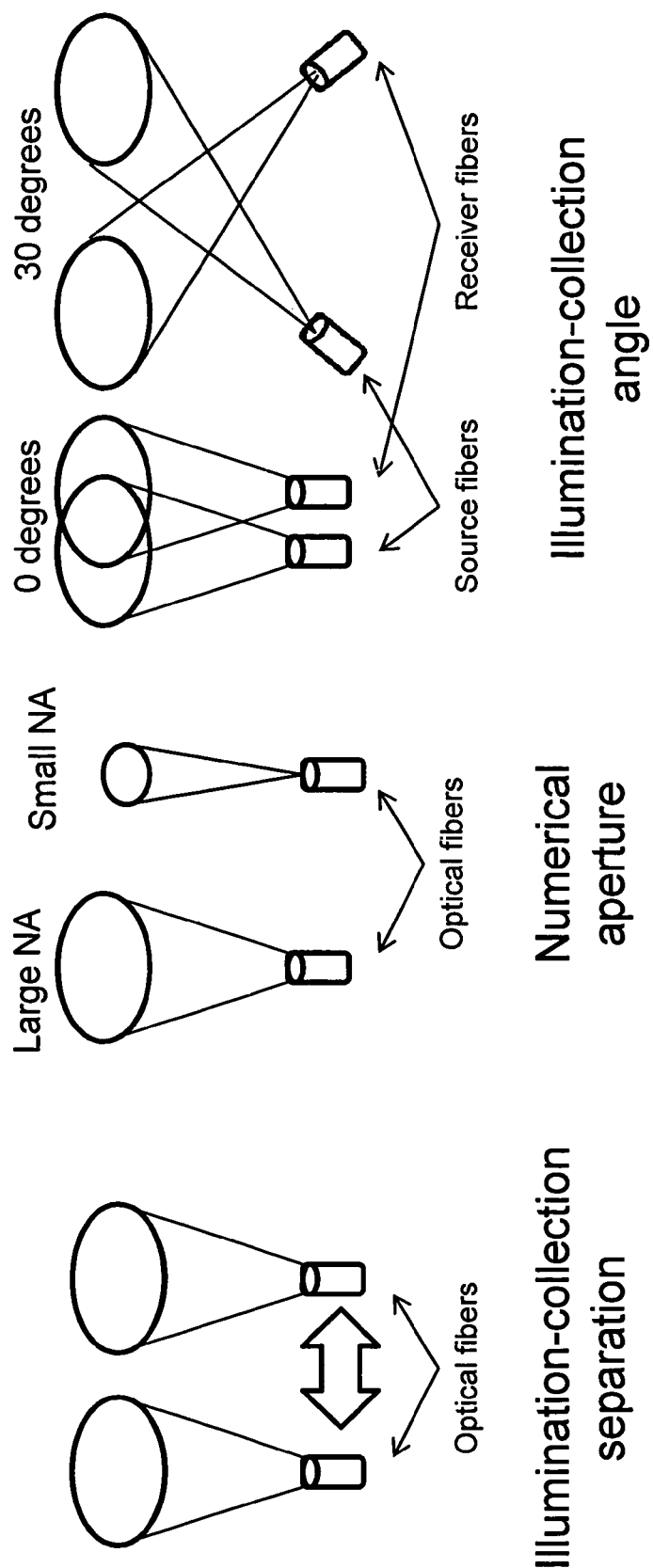
FIG. 6 depicts the parameters that collectively form an optical probe orientation.

Another aspect of the sampling subsystems is to use one or more channels where a channel refers to a specific orientation of the illumination and collection fibers. An orientation is comprised of the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 6 is a diagram of the parameters that form an orientation. Multiple channels can be used in conjunction, either simultaneously or serially, to improve the accuracy of the noninvasive measurements.

Figure 7:
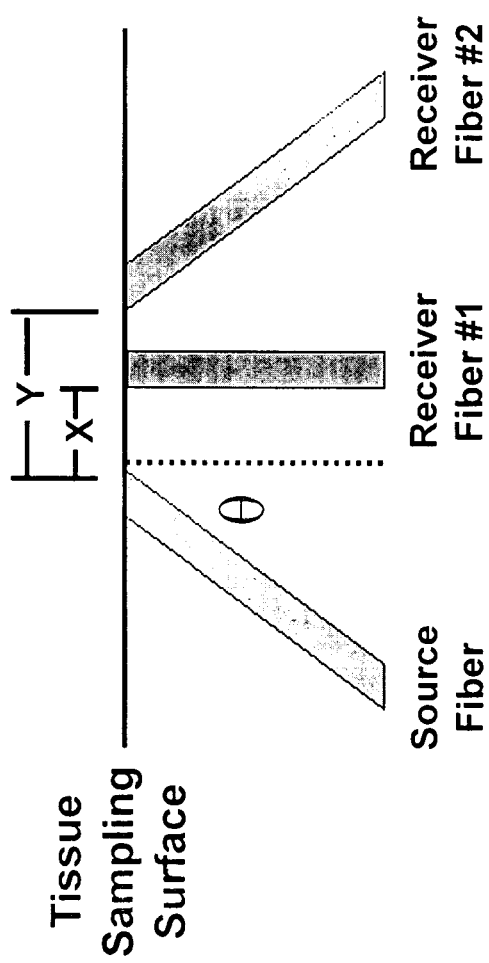
FIG. 7 shows an example embodiment of a two channel optical probe.

FIG. 7 is a diagram of a two channel sampling subsystem. In this example, the two channels are measuring the same tissue structure. Therefore each channel provides a measurement of the same tissue from a different perspective. The second perspective helps to provide additional spectroscopic information that helps to decouple the signals due to scattering and absorption. Referring to FIG. 7, the group of fibers (1 source, 1 receiver #1, and 1 receiver #2 in this example) can be replicated 1 to N times in order to increase the sampler area and improve optical efficiency. Each of the fibers can have a different numerical aperture and angle (θ). The distances between fibers, X and Y, determine the source-receiver separation. Furthermore, an additional source channel can be added that creates a 4-channel sampling subsystem. One skilled in the art recognizes the large number of possible variants and geometries with a multichannel sampling subsystem.

Figure 8:
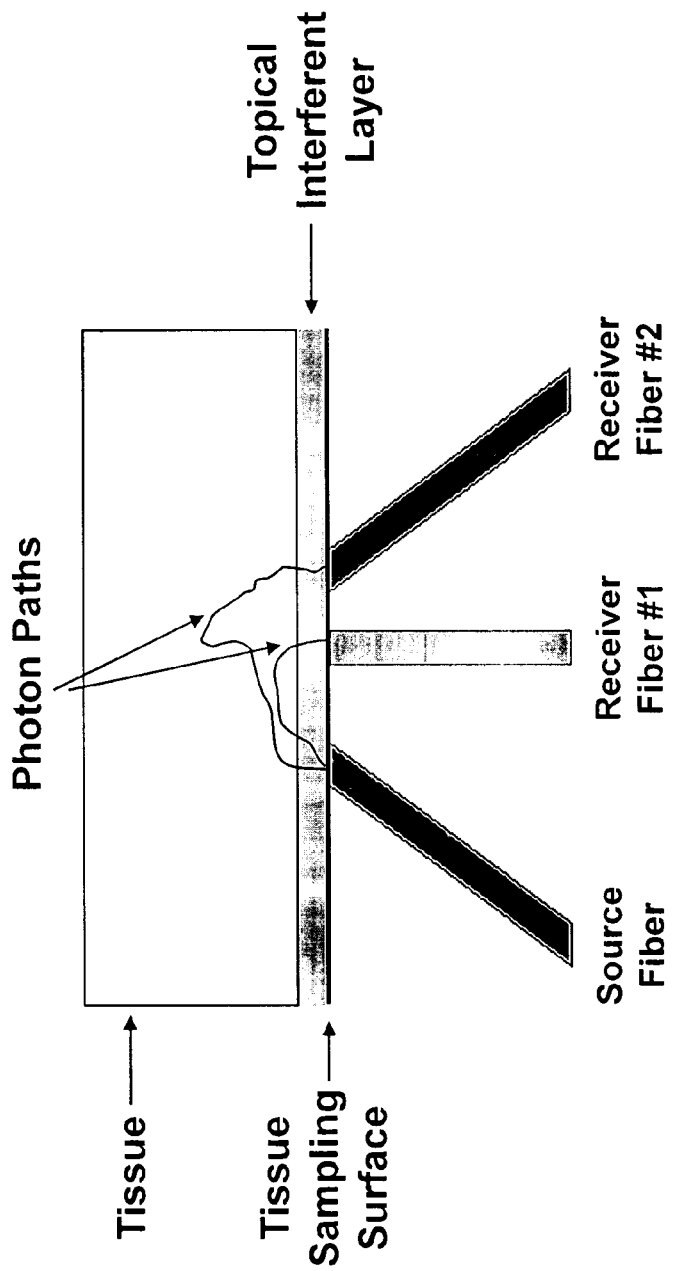
FIG. 8 is a diagram of the multiple channels sampling subsystem in the presence of a topical interferent.

One aspect of a multiple channel sampling subsystem is the ability to improve detection and mitigation of topical interferents, such as sweat or lotion, present on the sample. FIG. 8 is a diagram of the multiple channel sampling subsystem in the presence of a topical interferent. The figure shows the sampling subsystem at the tissue interface, a layer of topical interferent, and the tissue. In this example the contribution to each channel's measurement (i.e., the optical path length) due to the topical interferent is substantially identical. This allows the potential to decouple the common topical interferent signal present in both channels from the tissue signal that will be different for the two channels.

In other embodiments of the optical probe, the illumination and collection functions are performed by the same optical fibers. In this case, a pair of dichroic mirrors can be used to create a coaxial path for the light from the illumination subsystem and the light collected from the sample. A final lens focuses the excitation radiation and then collects and collimates Raman emission. The Raman emission passes through the second of the dichroic pair and a line blocking filter rejects Rayleigh scattered light. A lens couples the remaining light into an optical fiber or fiber bundle for relay to the spectrometer system.

Embodiments of optical probes that do not include optical fibers are also suitable for the present invention. For example, a system of light pipes, lenses, and/or mirrors (e.g. parabolic mirrors) can be used to convey light from the illumination subsystem to the sample and then collect light from the tissue and relay it to the spectrometer subsystem. As with the optical fiber based systems, line pass filters can be used to suppress or eliminate unwanted light prior to the illumination of the sample. One or more high pass filters can also be incorporated between the sampling surface and the spectrometer subsystem in order to suppress unwanted short-wavelength radiation as well as any Rayleigh scattered radiation.

Regardless of the components and materials used in its fabrication, an important aspect of the optical probe is that it can be designed in a manner that targets the compartments of the tissue pertinent to the attribute of interest, and can discriminate against light that does not travel a significant distance through those compartments. As an example, a 100 µm gap between illumination and collection optical fibers can discriminate against light that travels short distances through tissue and therefore contains little attribute information. In addition, the tissue interface can average over a certain area of the tissue to reduce errors due to the spatially heterogeneous nature of the tissue. The tissue sampling interface can reject specular and short pathlength rays and it can collect the portion of the light that travels the desired pathlength through the tissue with high efficiency in order to maximize the net attribute signal of the system. The tissue sampling interface can employ optical fibers to channel the light from the input to the tissue in a predetermined geometry as discussed above. The optical fibers, or other optical elements, can be arranged in a pattern that targets certain layers of the tissue (e.g. the dermis) that contain good attribute information. The spacing, angle, numerical aperture, and placement of the input and output fibers or optical elements can be arranged in an optimal manner to achieve effective depth targeting. Confocal Raman spectroscopy is a another example of depth targeting that can be suitable in the present invention.

Embodiments of the Ergonomic Apparatus

The present invention is suitable to measure different locations on the body, such as the forearm, the fingers, thumb, palm, wrist, or other accessible skin surfaces. Each site can benefit from reproducible placement and orientation relative to the optical surface of the sampling subsystem. An ergonomic apparatus can help achieve reproducible placement and orientation by mechanically guiding the site onto the optical surface. The ergonomic apparatus can either be an integral part of the device, or attached to the tissue location of interest. In the latter case, the device would then provide a means for interfacing with the ergonomic apparatus rather than the tissue. Additional details of each case are discussed below.

Figure 9:
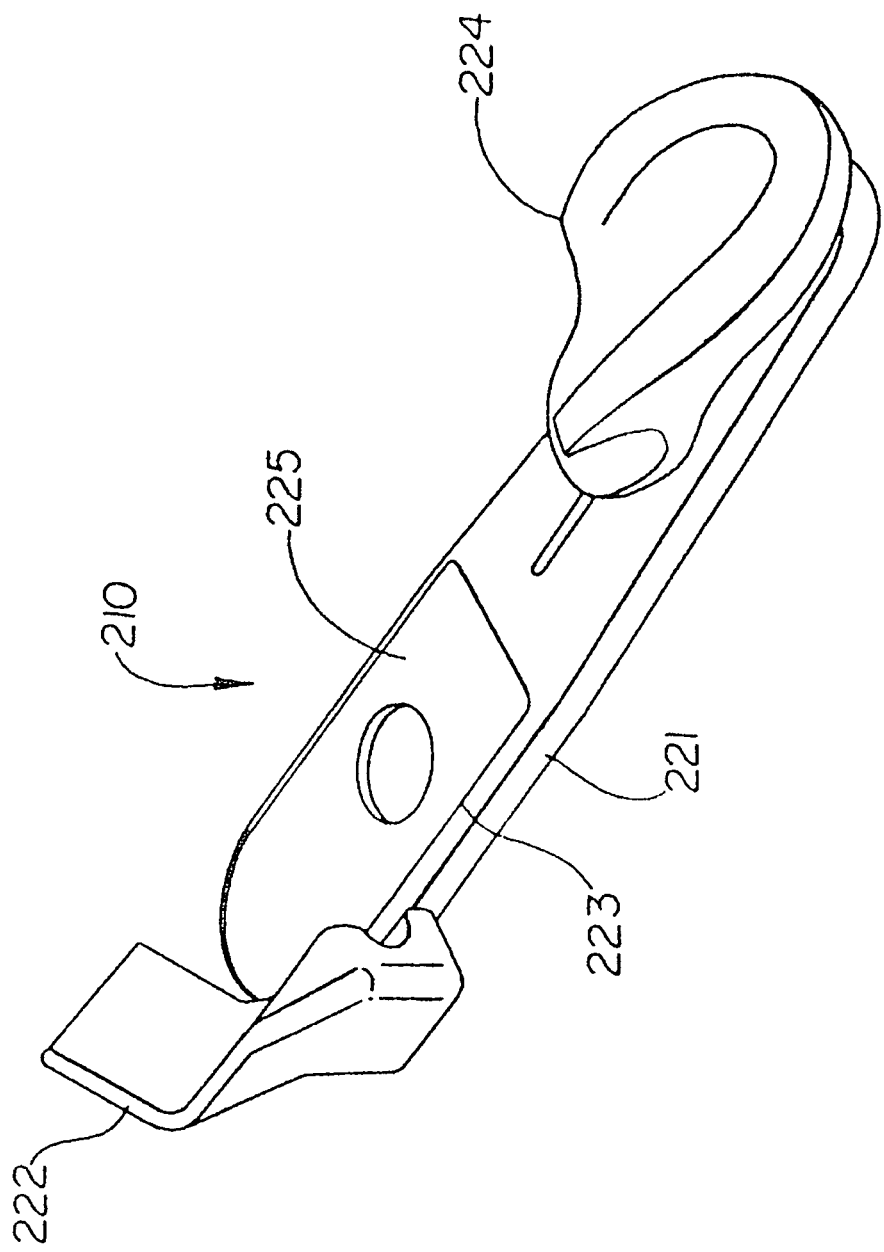

An example ergonomic apparatus 210 is depicted in FIG. 9. The tissue sampling subsystem can employ an ergonomic apparatus or cradle 210 that positions the tissue over the sampling interface 206 in a reproducible manner. In the case of sampling the underside of the forearm, an ergonomic cradle design is essential to ensure good contact with the sampling interface. The ergonomic cradle 210 includes a base 221 having an opening 223 therethrough. The opening is sized for receiving the sample head 216 therein to position the sampling surface 204 generally coplanar with an upper surface 225 of the base 221. The ergonomic cradle 210 references the elbow and upper arm of the subject via a bracket 222 in conjunction with a float-to-fit handgrip 224 to accurately position the forearm on the tissue sampling interface. Careful attention must be given to the ergonomics of the tissue sampling interface or significant sampling error can result.

In an example embodiment, the ergonomic cradle 210 is designed such that the forearm of the subject is reliably located over the sampling head 216. The bracket 222 forms an elbow rest that sets the proper angle between the upper arm and the sampling head 216, and also serves as a registration point for the arm. The adjustable hand rest 224 is designed to hold the fingers in a relaxed manner. The hand rest position is adjusted for each subject to accommodate different forearm lengths. In some embodiments, a lifting mechanism is included which raises and lowers the cradle periodically during sampling to break and reform the tissue interface. Reformation of the interface facilitates reduction of sampling errors due to the rough nature and heterogeneity of the skin. Alternate sites, for example fingertips, can also be accommodated using variations of the systems described herein.

An alternative to the ergonomic cradle is diagramed in FIG. 10. Instead of a cradle located on the measurement system, a positioning device can be located on the tissue. The positioning device can either be reusable or disposable and is adhered to the tissue with medical adhesive. The positioning device can also include an optically transparent film or other material that prevents physical contact with the sampling subsystem while preserving the desired optical characteristics of the measurement. The positioning device interfaces to the sampling subsystem in a pre-determined manner, such as alignment pins, in order to reproducibly locate the tissue to the sampling subsystem. The positioning device also prevents movement of the tissue relative to the sampling subsystem during the measurement process.

Other Aspects of the Sampling Subsystem

In some embodiments of the sampling subsystem, a device that thermostats the tissue interface is included and, in some embodiments, an apparatus that repositions the tissue on the tissue interface in a repetitive fashion is included. In other embodiments, an index matching fluid can be used to improve the optical interface between the tissue and sampling surface. The improved interface can reduce error and increase the efficiency, thereby improving the net attribute signal.

Spectrometer Subsystem

While other forms are suitable for the present invention, the embodiments of the spectrometer subsystem generally take one of two forms: dispersive or interferometric/modulating. While either form is suitable for the present invention, the chosen form depends largely on the excitation wavelength of the laser used in the illumination subsystem. The application of each spectrometer form in embodiments of Raman based alcohol monitors are discussed below.

Dispersive Raman Spectrometers

Dispersive spectrometers spatially separate different wavelengths of light using refraction or diffraction. Prisms, transmission gratings, and reflection gratings are all suitable dispersive elements for the present invention. A grating can be ruled or holographic, planar or concave. In all cases, different wavelengths of light are spatially separated (usually by exiting the dispersive element at different angles). The light is then imaged onto a focal plane such that each wavelength is located in a different spatial location. The optical design of the dispersive spectrometer is important, as the grating and other optical elements (e.g. collimating and condensing optics) determine the size and spatial resolution of the focal plane, the overall throughput of the spectrometer (a significant parameter that determines the signal to noise ratio of the system), and the interface between the output of the sampling subsystem and the input of the spectrometer subsystem. One skilled in the art recognizes that different optical configurations will result in different combinations of these figures of merit. Depending on the performance requirements of a given application, different resolutions or optical designs may be required.

Figure 11:
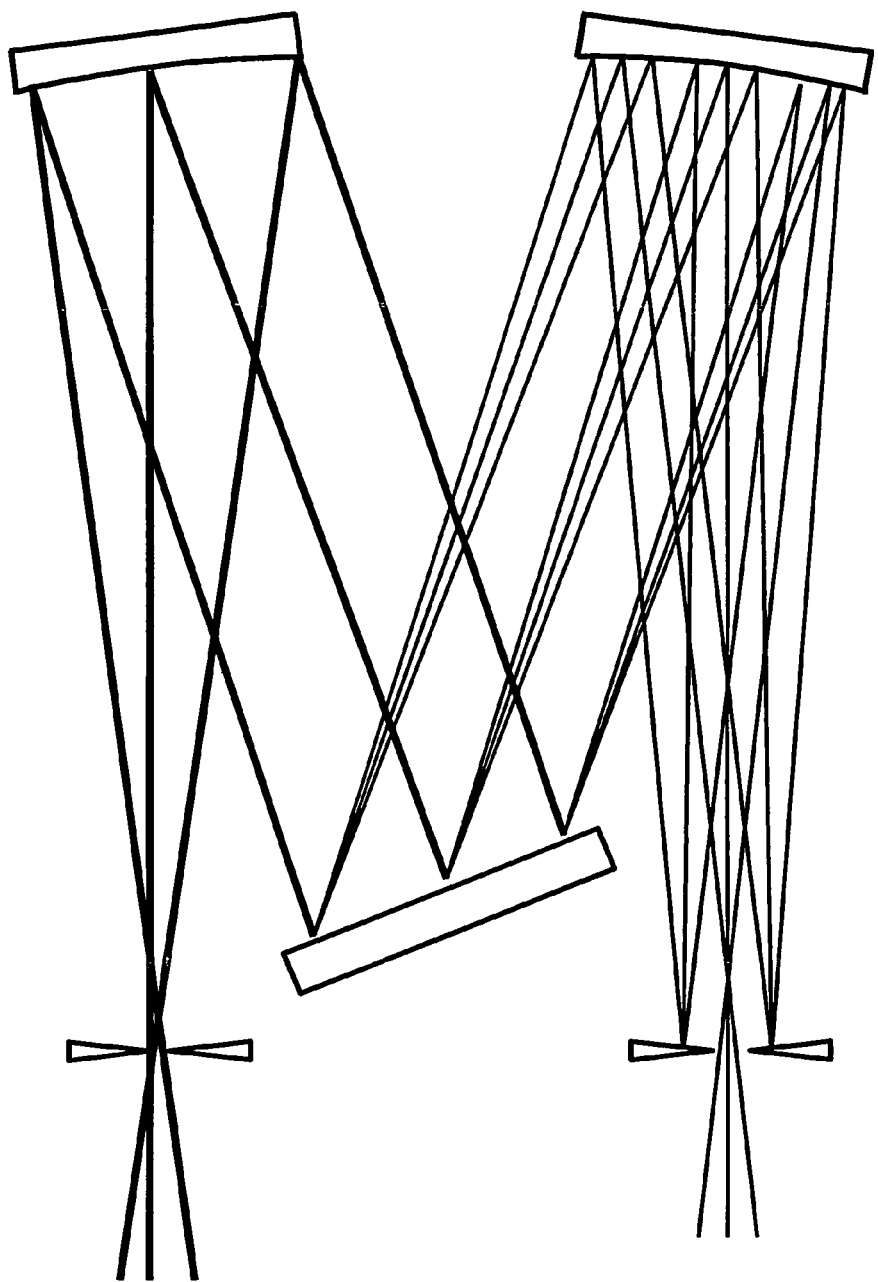
FIG. 11 shows the general configuration of a Czerny-Turner dispersive spectrometer.

There are several common geometries for dispersive spectrometers. A Czerny-Turner geometry is discussed herein for demonstrative purposes and is not intended to be limiting. FIG. 11 shows the general configuration of a Czerny-Turner dispersive spectrometer.

The Czerny-Turner (and other) geometry gives rise to multiple detection configurations. As each wavelength is imaged at a different location on the focal plane, multiple detectors can be used to detect more than one wavelength at a given time. This is typically accomplished by an array detector such as a multi-element CCD in the visible region of the electromagnetic spectrum. Several other detector types are viable depending on the region of interest. Some commonly encountered examples include Silicon, CID's, InGaAs, InAs, InSb, Ge, PbS, PbSe, PtSi, PMT, and MCT.

Alternatively, a single detector can be used and the dispersive element rotated to "scan" through each wavelength of interest. As with array detection above, multiple detector types are suitable depending on the specific embodiment under consideration. Combinations of scanning and array detection are also possible. For example, the dispersive element could be oriented to image a specific region onto an array detector thereby measuring all wavelengths of interest in that region simultaneously. The array could then be moved or rotated to image a different region onto the same array. Furthermore, multiple dispersive elements could be used simultaneously (e.g. echelles) or in sequence. Dispersive spectrometers offer the potential advantage of no moving parts, multiplexing (measurement of multiple wavelengths simultaneously), and the ability to reject Rayleigh light by ensuring the image of its wavelength falls off of the array or single element detector.

Modulating/Interferometric Raman Spectrometers

Figure 12:
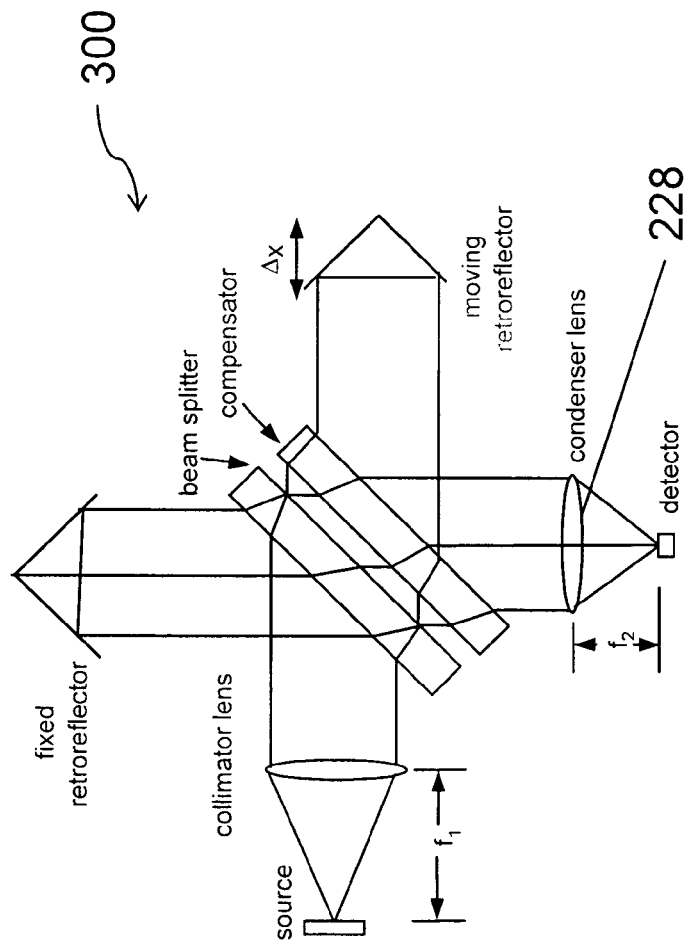
FIG. 12 shows a lens as a part of the spectrometer subsystem that collimates the light from the sampling subsystem.

In some example embodiments using a Modulating/Interferometric spectrometer, the light obtained from the sampling subsystem is collimated. This can be accomplished using any combination of refractive and/or reflective optics. In some embodiments, the light collected by the sampling subsystem is collimated by a plano-aspheric lens made of ZnSe. The design of the lens is such that the collimated beam has less than five degrees of divergence. This lens 228 is schematically depicted in FIG. 12 as part of a spectrometer subsystem 300. The collimating lens 228 produces a beam with low optical distortion that serves as the proper input to the FT spectrometer discussed below.

Figure 13:
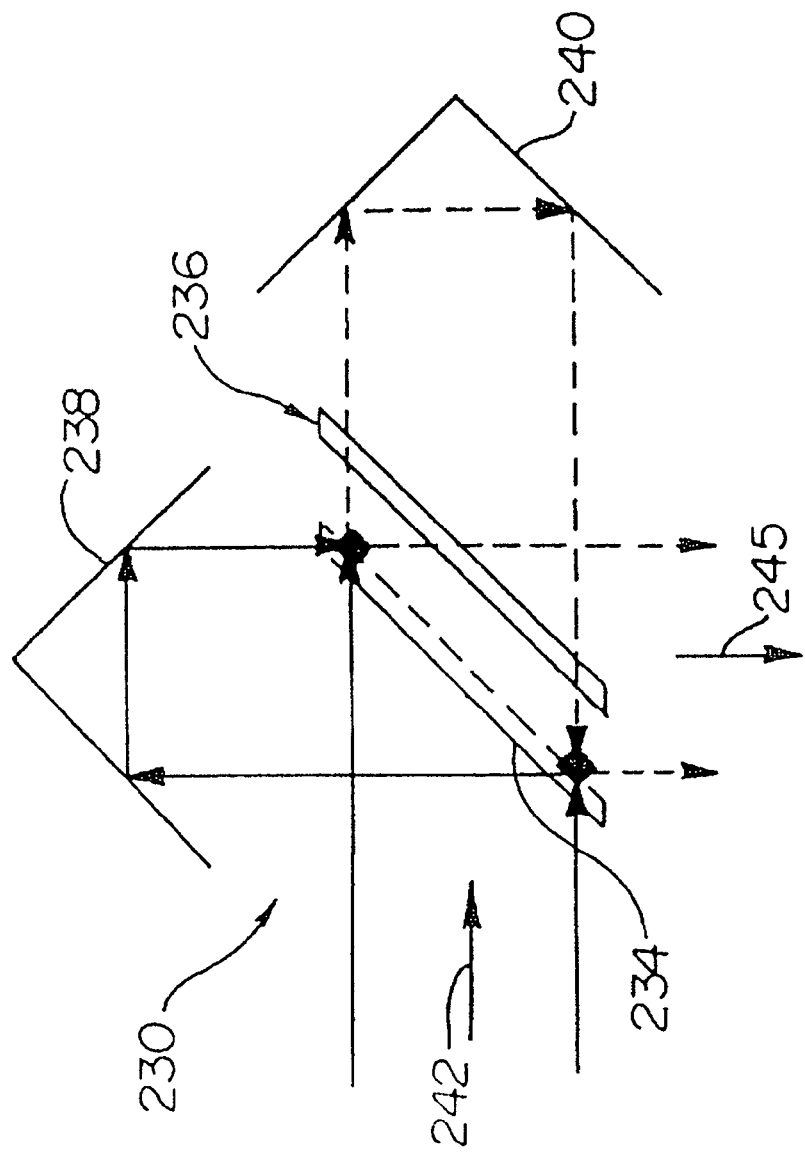
FIG. 13 shows the general configuration of a Michelson geometry Fourier Transform spectrometer.

In some embodiments of the spectrometer subsystem 300, a Fourier Transform (FT) spectrometer 230 is used. The FT spectrometer modulates the collimated light from the sampling subsystem 200 to create an interferogram that contains all of the spectral information of interest. FIG. 13 schematically depicts one embodiment of an FT spectrometer 230 which includes a beamsplitter 234 and compensator optics 236, a fixed retro-reflector 238 and a moving retro-reflector 240. The collimated input light 242 impinges on the beamsplitter optic 234 and is partially reflected and partially transmitted by the coating on the back surface of the beamsplitter 234. The reflected light passes back through the beamsplitter optic 234 and reflects off the fixed retro-reflector 238 and back to the beamsplitter 234. The transmitted light passes through the compensator optic 236 and reflects off the moving retro-reflector 240 and back to the beamsplitter 234. The transmitted and reflected portions of the light recombine at the beamsplitter to create an interference pattern or interferogram. The amount of constructive and/or destructive interference between the transmitted and reflected beams is dependent on the spectral content of the collimated input beam 242 and on the optical path difference between the fixed retro-reflector 238 and the moving retro-reflector 240. The recombined beams are then directed and focused onto an optical detector that converts the light into an electrical signal. Examples of suitable detectors for the present invention include, but are not limited to, CCD's, Silicon, CID's, InGaAs, InAs, InSb, Ge, PbS, PbSe, PtSi, and MCT.

Figure 14:
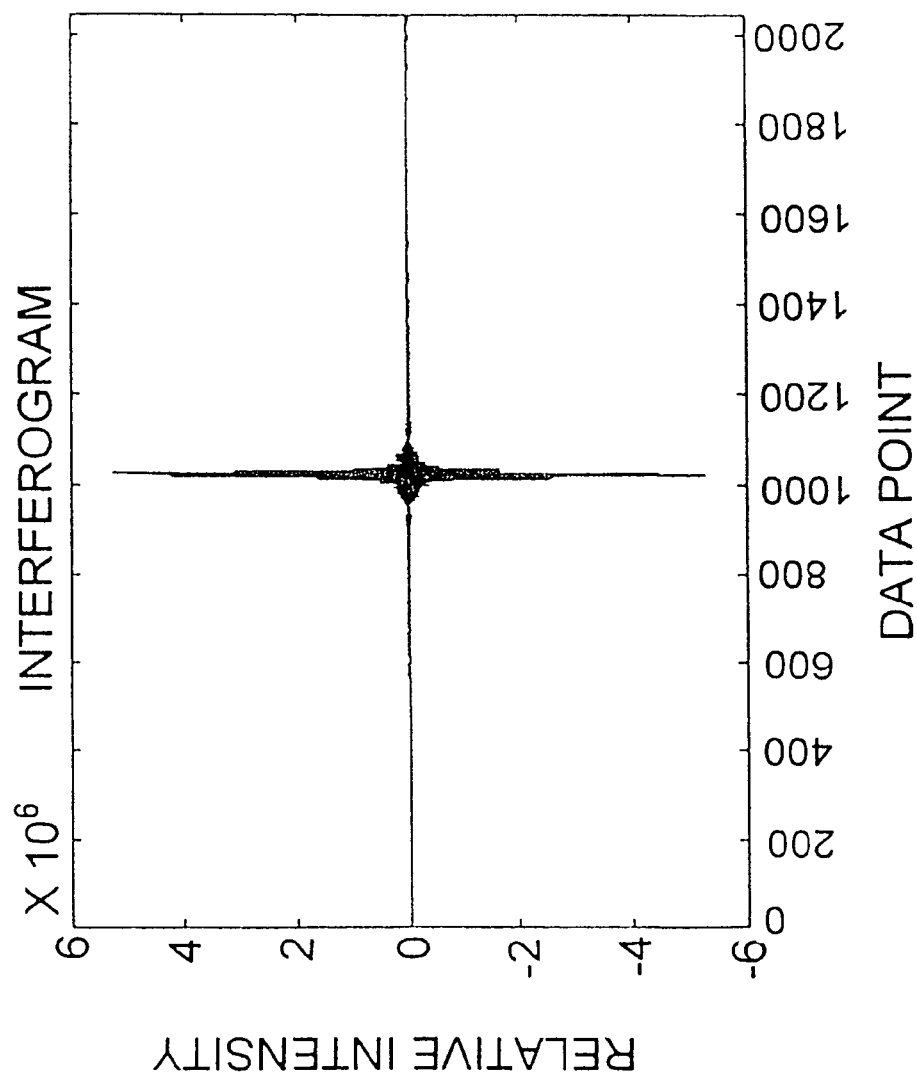
FIG. 14 shows a typical digitized interferogram created by an FT spectrometer.

The electrical signal is then digitized using appropriate analog and digital circuitry. FIG. 14 shows a typical digitized interferogram created by an FT spectrometer. At the point of zero path difference between the transmitted and reflected beams, there will be maximum constructive interference, and the centerburst of the interferogram is created. The spectral resolution imparted by an FT spectrometer depends in part on the distance travelled by the moving mirror. Depending on the performance required for a given embodiment, resolutions from $0.1$ cm$^{-1}$ to $128$ cm$^{-1}$ can be suitable.

A reference laser can allow knowledge of the actual optical path difference as a function of time. Using the knowledge of the optical path difference, the infrared signal can be sampled in equal position increments to satisfy the requirements of a Fourier transform. Typically, a helium neon (HeNe) laser is used as the reference in interferometers because of its comparatively small size and cost relative to other gas lasers. A lower cost, solid state alternative to HeNe lasers is also suitable. See, e.g., U.S. Pat. No. 6,654,125, "Method and apparatus for optical spectroscopy incorporating a vertical cavity surface emitting laser (VCSEL) as an interferometer reference" (Maynard); U.S. patent application Ser. No. 10/678,843, "Optical spectroscopy incorporating a vertical cavity surface emitting laser (VCSEL)" (Abbink); U.S. patent application Ser. No. 11/611,603, "Optical Spectroscopy Incorporating A Vertical Cavity Surface Emitting Laser (VCSEL)" (Abbink); each of which is incorporated herein by reference.

The above described FT spectrometer an example of the broader class of interferometric/modulating spectrometers that are known in the art and is not intended to be limiting. One skilled in the art recognizes the wide variety of optical configurations and approaches that collectively fall under this category.

Other Modalities

While the examples described above generally concern steady-state Raman measurements it is possible to apply these methods to other Raman spectroscopy measurement modalities. Another suitable approach involves time-resolved techniques, in which a short burst of excitation light is applied to the tissue, and the Raman emission is time-gated as means to reject the 'slower' fluorescence. In addition, any of these techniques can be used in conjunction with an imaging methodology such as microscopy or macroscopic scanning of the excitation beam in order to acquire information about the spatial information. Any of the above-mentioned methods can be used in conjunction with a measurement technique that allows depth discrimination, such as a confocal detection system or optical coherence tomography, to add information concerning the distribution of Raman-active constituents with respect to depth beneath the tissue surface. The preceding discussion primarily describes detection of spontaneous Raman scattering as the means for gathering noninvasive, spectroscopic information relating to the disease state of the tissue. Other Raman techniques can also be incorporated in the invention. Examples of these alternative techniques are resonance Raman spectroscopy, surface-enhanced Raman scattering (SERS), anti-Stokes Raman scattering and coherent anti-Stokes Raman spectroscopy (CARS).

Computing Subsystem

Determining a Raman Emission Spectrum

Raman emission occurs when tissue inelastically scatters incident light. The wavelength difference between the incident and scattered light corresponds to the energy contributed to the vibrational energy of molecular constituents of the tissue. A Raman spectrum is the aggregate of wavelength-shifted, inelastically scattered radiation owing the specific structure and peaks to the chemical makeup of the tissue or sample under investigation. Raman spectra convey specific information about the vibrational, stretching, and breathing bond energies of the illuminated sample. This molecular specificity provides insight into tissue composition. While Raman spectroscopy is rich in information about the molecular composition of the tissue, it can be obscured by other optical phenomena such as fluorescence and Rayleigh (elastic) scattering. Line rejection filters (or similar) can be used to reduce interference from scattered incident light. Longer wavelength excitation sources can aid in reducing tissue fluorescence. Near infrared (NIR) excitation sources have the additional benefit of deeper penetration in tissue. Nevertheless, even using NIR excitation, tissue auto-fluorescence can be orders of magnitude more intense than the Raman scattering signal. Wavelength shift techniques or polynomial subtraction can be used to extract the comparatively weak Raman signal from the large, broad fluorescence spectra. See Shim and Wilson, J Raman Spectroscopy, 1997 and references cited therein.

When excitation light is launched into the tissue, it is subject to scattering and absorption processes that vary with the optical properties of the site under interrogation, the excitation wavelength, and the optical probe geometry. Emitted Raman light is also subject to wavelength- and location-dependent absorption and scattering as it propagates through the tissue prior to emergence and collection. Often, the tissue property of interest is its 'intrinsic' Raman emission, defined as the Raman emission that is scattered by a specimen that is homogeneous, non-scattering, and optically dilute. In order to accurately characterize the intrinsic Raman spectrum of the tissue of interest, the spectra-altering effects of scattering and absorption that are impressed upon the excitation and emitted light can be removed. Variations due to subject-to-subject and site-to-site differences can overwhelm the subtle spectral variations indicative of tissue status. Spectral correction based upon the tissue optics of each subject (at the same site as the Raman measurement, or at a different site having a predictable relationship to the site) can reveal the intrinsic Raman spectra of the molecules of interest. This intrinsic correction mitigates the variations across and within subjects, unmasking the spectral features relating to presence and state of disease.

Figure 15:
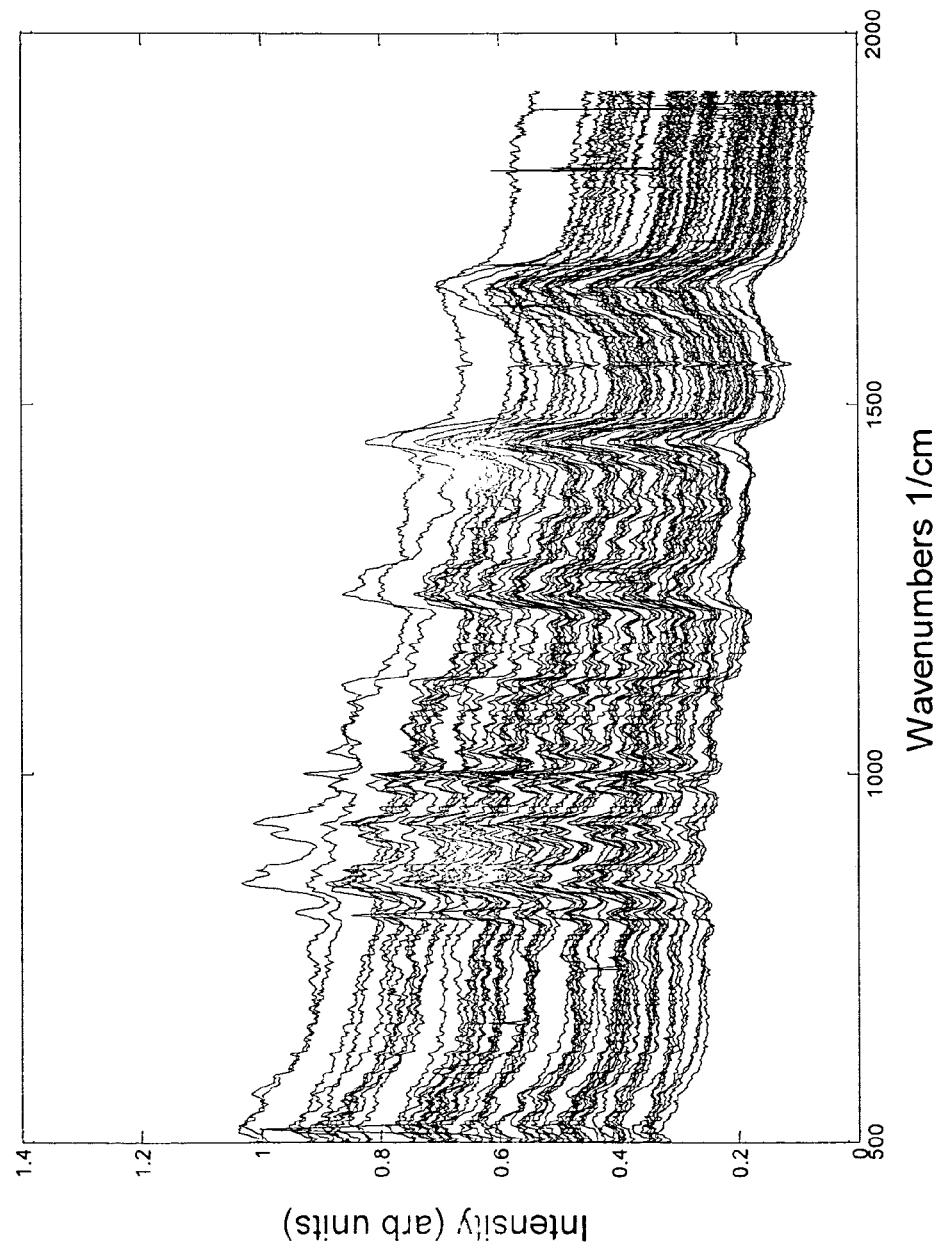
FIG. 15 shows typical measured Raman spectra of skin.

Typical measured Raman spectra of skin are shown in FIG. 15. The spectra demonstrate typical variations resulting from imperfect probe repositioning, environmental changes and subject-to-subject physiological differences. These variations can exceed the spectral variations due to alcohol concentration and hamper the utility of the measured spectra. In order to accurately determine alcohol concentration, additional tissue-specific spectral corrections can be applied to obtain the intrinsic tissue Raman emission. One approximation for estimating the intrinsic spectrum, $E_{corr}$, involves dividing the measured Raman spectrum by the product of the roots of the measured reflectance at the excitation and/or emission wavelengths. See, e.g., Finlay et al., Photochem Photobiol, 2001, and Wu et al., Appl Opt, 1993:

$$E_{corr}(\lambda_x, \lambda_m) = \frac{E_{meas}(\lambda_x, \lambda_m)}{R_{meas}(\lambda_x)^k R_{meas}(\lambda_x)^n}; n, k < 1 \quad \text{Eq 1}$$

The optimum values for n and k are dependent on the arrangement of source and detector fibers, and can be determined empirically.

If multiple spectra are collected from each sample at an acquisition session, then the spectroscopic insertion variation, $S_{insert}$ of the ith spectrum for specimen j can be expressed as the absolute deviation of that spectrum from the specimen's median:

$$S_{insert_{i,j}}(\lambda,n,k) = abs[E_{corr_{i,j}}(\lambda,n,k) - \text{median}(E_{corr\cdot j}(\lambda,n,k))]/\text{median}(E_{corr\cdot j}(\lambda,n,k)). \quad \text{Eq 2}$$

An aggregate measure of insertion variation is then the variance of $S_{insert}$:

$$v_{insert}(\lambda,n,k) = \text{var}(S_{insert}(\lambda,n,k)). \quad \text{Eq 3}$$

A variety of other procedures can accomplish intrinsic spectral correction. For example, a number of methods by which the measured spectra can be corrected using knowledge of the measured reflectance, tissue optical properties, and probe-dependent parameters can be used with the present invention. See, e.g., Gardner et al., Appl Opt, 1996, Zhang et al., Opt Lett, 2000; Muller et al., Appl Opt, 2001. In addition, intrinsic corrections can be made using a procedure in which the correction parameters for a given probe are created by measuring one or more tissue phantoms for which the emission, absorption, and scattering properties have been well characterized. This procedure can also be accomplished via Monte-Carlo or other computer simulation of the optical probe's response to media with known optical properties. Any of these processes can be used to correct for the effects of tissue optical properties in noninvasive skin Raman emission measurements.

Determining the Quality of the Raman Emission Spectrum and the Analyte Property of Interest Regardless of the specific embodiment of the spectrometer subsystem, the computer system can check the acquired spectra for outliers. An outlier spectrum is one that violates the hypothesized relationship between the measured signal and the properties of interest. Examples of outlier conditions include conditions where the calibrated instrument is operated outside of the specified operating ranges for ambient temperature, ambient humidity, vibration tolerance, component tolerance, power levels, etc. In addition, an outlier can occur if the composition or concentration of the sample is different than the composition or concentration range of the samples used to build the calibration model. The calibration model will be discussed as part of the calibration subsystem later in this disclosure. Any outlier spectra can be deleted and the remaining good spectra can be averaged together or individually stored for later use.

The accepted spectra are then used to determine the attribute of interest in conjunction with the calibration model that is obtained from the calibration subsystem 500. After determination of the attribute of interest, the computing subsystem 400 can report the result to the subject. The computing subsystem 400 can also report the level of confidence in the goodness of the result. If the confidence level is low, the computing subsystem 400 can withhold the result and ask the subject to retest. If required, additional information can be conveyed that directs the user to perform a corrective action. See, e.g. U.S. patent application Ser. No. 10/410,006, "Reduction of errors in non-invasive tissue sampling" (Maynard), incorporated herein by reference. The results can be reported visually on a display, by audio and/or by printed means. Additionally, the results can be stored to form a historical record of the attribute. In other embodiments, the results can be stored and transferred to a remote monitoring or storage facility via the internet, phone line, or cell phone service.

The computing system 400 can also contain a communication link that allows transfer of a subject's measurement records and the corresponding spectra to an external database. In addition, the communication link can be used to download new software to the computer and update the multivariate calibration model. The computer system can be viewed as an information appliance. Examples of information appliances include personal digital assistants, web-enabled cellular phones and handheld computers.

Calibration Subsystem

Determination of the Relationship Between Raman Spectra and Alcohol Concentration The relationship between tissue Raman spectral properties at one or more wavelengths and alcohol concentration may not be apparent upon visual inspection of the spectral data. Because this is the case, it is usually necessary that a multivariate mathematical relationship, or 'model', be constructed to classify attributes or to quantify chemical changes using intrinsic Raman spectra. The construction of such a model generally occurs in two phases: (i) collection of 'calibration' or 'training' data, and (ii) establishing a mathematical relationship between the training data and the attribute or reference concentrations represented in the training data.

During the collection of training data, it can be desirable to collect Raman data from many individuals that span a range of demographic conditions. Furthermore, these data should be collected over a variety of environmental conditions consistent with those expected in future use as well as over a range of concentrations for the analyte of interest (e.g. alcohol concentration). It can be important to collect these data in a manner that minimizes the correlation between alcohol concentration and other parameters that can result in spectral variation. The multivariate calibration model can empirically relate known alcohol concentrations in a set of calibration samples to the measured spectral variations obtained from the calibration samples. This relationship can then be applied to subsequent measurements Partial Least Squares (PLS) regression is a well established multivariate analysis method that has been applied to quantitative analysis of spectroscopic measurements and will be used for demonstrative purposes for the remainder of the disclosure. However, other multivariate analysis methods such as Principal Components Regression (PCR), Ridge Regression, Multiple Linear Regression (MLR) and Neural Networks are equally suitable for the present invention. One skilled in the art will recognize that other methods of similar functionality are also applicable.

In PLS regression, a set of spectroscopic calibration measurements is acquired where each has a corresponding reference value for the property of interest (e.g. blood alcohol concentration). The calibration spectral data are then decomposed into a series of factors (spectral shapes that are sometimes called loading vectors or latent variables) and scores (the magnitude of the projection of each spectrum onto a given factor) such that the squared covariance between the reference values and the scores on each successive PLS loading vector is maximized. The scores of the calibration spectra are then regressed onto the reference values in a multiple linear regression (MLR) step in order to calculate a set of spectral weights (one weight per wavenumber in the spectra) that minimizes the analyte measurement error of the calibration measurements in a least-squares sense. These spectral weights are called the regression vector of the calibration model. Once the calibration model is established, subsequent measurements are obtained by calculating the vector dot product of the regression vector and each measured spectrum.

The primary advantage of PLS and similar methods (commonly referred to as indirect methods) is that complete characterization of the sample and acquired spectra is not required (e.g. concentrations and identities of other constituents within the samples do not need to be known). Furthermore, inverse methods tend to be more robust at dealing with nonlinearities in the spectral measurement such as those caused by instrumental drift, light scattering, environmental noise, and chemical interactions.

Functionally, the goal of the multivariate calibration (PLS or otherwise) in the present invention is to determine the part of the spectroscopic signal of alcohol that is effectively orthogonal (contravariant) to the spectra of all interferents in the sample. This part of the signal is referred to as the net attribute signal and can be calculated using the regression vector (b) described above using equation 4. If there are no interfering species, the net attribute spectrum is equal to the pure spectrum of alcohol. If interfering species with similar spectra to the attribute are present, the net attribute signal (NAS) will be reduced relative to the entire spectrum.

$$NAS = \frac{\hat{b}}{\|\hat{b}\|_2^2} \qquad \text{Eq 4}$$

Alternative calibration strategies can be used in place of, or in conjunction with, the above described methods. For example, in some embodiments biometric enrollment information is acquired from each person who is authorized to use a given piece of machinery or vehicle. In such cases, the enrollment measurements can also be used to improve the accuracy and precision of the alcohol or substance of abuse measurement. In this scenario, the calibration spectra can be mean-centered by subject (all spectra from a subject are located, the mean of those spectra is subtracted from each, and the "mean centered" spectra are returned to the spectral set). In this manner, the majority of inter-subject spectral differences caused by variations in physiology are removed from the calibration measurements and the range of spectral interferents correspondingly reduced. The centered spectra and associated analyte reference values (blood alcohol concentrations) are then presented to a multivariate analysis method such as partial least squares regression. This process is referred to as generating an "enrolled", "generic", or "tailored" calibration. Additional details on this approach are described in U.S. Pat. No. 6,157,041, entitled "Methods and Apparatus for Tailoring Spectroscopic Calibration Models," incorporated by reference.

In practice, once a future, post calibration, subject is enrolled on a noninvasive device their enrollment spectrum can be subtracted from subsequent measurements prior to determining the alcohol, alcohol byproduct, or substance of abuse concentration using the generic calibration model. Similar to the mean-centering by subject operation of the calibration spectra, the subtraction of the enrollment spectrum removes the average spectroscopic signature of the subject while preserving the signal of the analyte of interest (alcohol or substance of abuse). In some embodiments, significant performance advantages can be realized relative to the use of a non-generic calibration method.

Once formed, a calibration (generic or otherwise) should remain stable and produce accurate attribute predictions over a desired period of time. This process is referred to as calibration maintenance and can comprise multiple methods that can be used individually or in conjunction. The first method is to create the calibration in a manner that inherently makes it robust. Several different types of instrumental and environmental variation can affect the measurement capability of a calibration model. It is possible and desirable to reduce the magnitude of the effect of instrumental and environmental variation by incorporating this variation into the calibration model.

Calibration Maintenance and Transfer

It is difficult, however, to span the entire possible range of instrument states during the calibration period. System perturbations can result in the instrument being operated outside the space of the calibration model. Examples of potentially problematic instrument and environmental variation include, but are not limited to, changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system. Measurements made while the instrument is in an inadequately modeled state can exhibit measurement errors. In the case of in vivo optical measurements of analyte properties, these types of errors can result in erroneous measurements that degrade the utility of the system. Therefore it is often advantageous to use additional calibration maintenance techniques during the life of the instrument in order to continually verify and correct for the instrument's status.

Calibration maintenance techniques are discussed in commonly assigned U.S. patent application Ser. No. 09/832,608, "Optically Similar Reference Samples and Related Methods for Multivariate Calibration Models Used in Optical Spectroscopy," and U.S. patent application Ser. No. 10/281,576, "Optically Similar Reference Samples," and U.S. patent application Ser. No. 10/733,195, "Adaptive Compensation for Measurement Distortions in Spectroscopy," each of which is incorporated herein by reference. These methods use an environmentally inert non-tissue sample, such as an integrating sphere, that optionally contains the attribute of interest, in order to monitor the instrument over time. The sample can be incorporated into the optical path of the instrument or interface with the sampling subsystem in a manner similar to that of tissue measurements. The sample can be used in transmission or in reflectance and can contain stable spectral features or contribute no spectral features of its own. The material can be a solid, liquid, or gel material as long as its spectrum is stable or predictable over time. Any unexplained change in the spectra acquired from the sample over time indicate that the instrument has undergone a perturbation or drift due to environmental effects. The spectral change can then be used to correct subsequent tissue measurements in humans in order to ensure and accurate attribute measurement.

Once a calibration is formed, it is desirable to transfer the calibration to existing and future instruments. This process is commonly referred to as calibration transfer. While not required, calibration transfer prevents the need for a calibration to be built on each system that is manufactured. This represents a significant time and cost savings that could result in the difference between success or failure of a commercial product. Calibration transfer arises from the fact that optical and electronic components vary from unit to unit which, in aggregate, results in differences in the spectra obtained from multiple instruments. For example, the responsivity of two detectors can also differ significantly, which can result in spectral differences between instruments.

Similar to calibration maintenance, multiple methods can be used in order to effectively achieve calibration transfer. The first method is to build the calibration with multiple instruments. The presence of multiple instruments allows the spectral variation associated with instrument differences to be determined and made effectively orthogonal to the attribute signal during the calibration formation process. While this does approach reduces the net attribute signal, it can be an effective means of calibration transfer.

Additional calibration transfer methods involve explicitly determining the difference in the spectral signature of a system relative to those used to build the calibration. In this case, the spectral difference can then be used to correct a spectral measurement prior to attribute prediction on a system or it can be used to correct the predicted attribute value directly. The spectral signature specific to an instrument can be determined from the relative difference in spectra of a stable sample acquired from the system of interest and those used to build the calibration. Many suitable approaches and algorithms for effective calibration transfer are known in the art; some of which are summarized in "Standardization and Calibration Transfer for Near Infrared Instruments: a Review", by Tom Fearn in the Journal of Near Infrared Spectroscopy, vol. 8, pp. 229-244 (2001). Note that these approaches and algorithms are equally suited to other spectroscopic techniques such as Raman measurements. The samples described in the calibration maintenance section can also be applicable to calibration transfer. See, e.g. U.S. Pat. No. 6,441,388, incorporated herein by reference.

Additional Aspects of the Present Invention
Calibration Check Samples

In addition to disposables to ensure subject safety, disposable calibration check samples can be used to verify that the instrument is in proper working condition. In many commercial applications of alcohol measurements, the status of the instrument must be verified to ensure that subsequent measurements will provide accurate alcohol concentrations or attribute estimates. The instrument status is often checked immediately prior to a subject measurement. In some embodiments, the calibration check sample can include alcohol. In other embodiments, the check sample can be an environmentally stable and spectrally inert sample, such as an integrating sphere. The check sample can be a gas or liquid that is injected or flowed through a spectroscopic sampling chamber. The check sample can also be a solid, such as a gel, that may contain alcohol. The check sample can be constructed to interface with the sampling subsystem or it can be incorporated into another area of the optical path of the system. These examples are meant to be illustrative and are not limiting to the various possible calibration check samples.

Direction of Change (DOC) and Rate of Change (ROC)

The present invention also comprises a method for measurement of the direction and magnitude of concentration changes of tissue constituents, such as alcohol, using spectroscopy. The non-invasive measurement obtained from the current invention is inherently semi-time resolved. This allows attributes, such as alcohol concentration, to be determined as a function of time. The time resolved alcohol concentrations can then be used to determine the rate and direction of change of the alcohol concentration. In addition, the direction of change information can be used to partially compensate for any difference in blood and non-invasive alcohol concentration that is caused by physiological kinetics. See, e.g., U.S. Pat. No. 7,016,713,"Non-invasive determination of direction and rate of change of an analyte" (Gardner); U.S. patent application Ser. No. 11/328,927, "Apparatus for non-invasive determination of direction and rate of change of an analyte" (Gardner), each of which is incorporated herein by reference. A variety of techniques for enhancing the rate and direction signal have been uncovered. Some of these techniques include heating elements, rubrifractants, and index-matching media. They should not be interpreted as limiting the present invention to these particular forms of enhancement or equilibration. These enhancements are not required to practice the present invention, but are included for illustrative purposes only.

Subject Safety

Another aspect of non-invasive alcohol measurements is the safety of the subjects during the measurements. In order to prevent measurement contamination or transfer of pathogens between subjects it is desirable, but not necessary, to use disposable cleaning agents and/or protective surfaces in order to protect each subject and prevent fluid or pathogen transfer between subjects. For example, in some embodiments an isopropyl wipe can be used to clean each subject's sampling site and/or the sampling subsystem surface prior to measurement. In other embodiments, a disposable thin film of material such as ACLAR could be placed between the sampling subsystem and the subject prior to each measurement in order to prevent physical contact between the subject and the instrument. In other embodiments, both cleaning and a film could be used simultaneously. As mentioned in the sampling subsystem portion of this disclosure, the film could also be attached to an positioning device and then applied to the subjects sampling site. In this embodiment, the positioning device would interface with the sampling subsystem and prevent the subject from moving during the measurement while the film serves its protective role.

Topical Interferents

Figure 16:
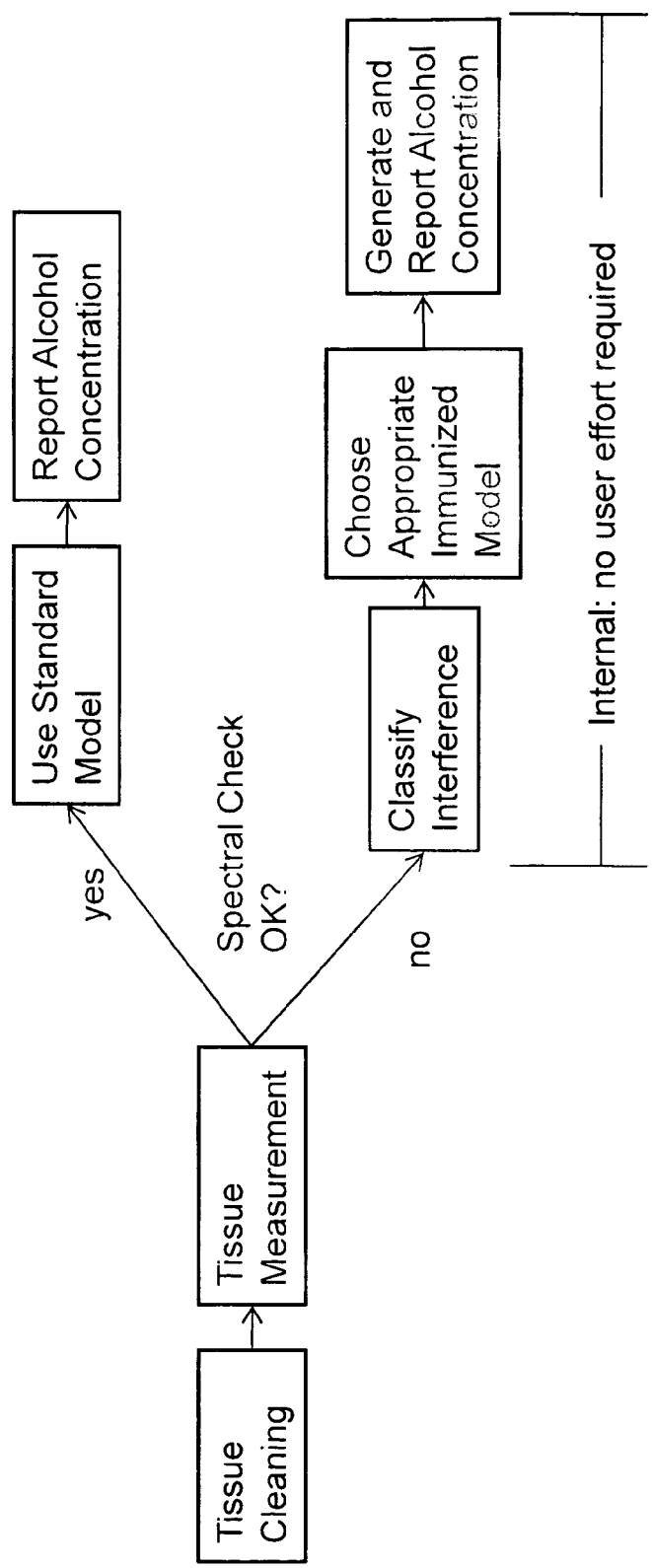
FIG. 16 shows a flow diagram that describes a method for combining the three topical interferent mitigation approaches into one combined process.

In subject measurements the presence of topical interferents on the sampling site is a significant concern. Many topical interferents have spectral signatures in the near infrared region and can therefore contribute significant measurement error when present. The present invention deals with the potential for topical interferents in three ways that can be used individually or in conjunction. FIG. 16 shows a flow diagram that describes a method for combining the three topical interferent mitigation approaches into one combined process. First, a disposable cleaning agent similar to that described in the subject safety section can be used. The use of the cleaning agent can either be at the discretion of the system operator or a mandatory step in the measurement process. Multiple cleaning agents could also be used that individually target different types of topical interferents. For example, one cleaning agent could be used to remove grease and oils, while another could be used to remove consumer goods such as cologne or perfume. The purpose of the cleaning agents is to remove topical interferents prior to the attribute measurement in order to prevent them from influencing the accuracy of the system.

Figure 17:
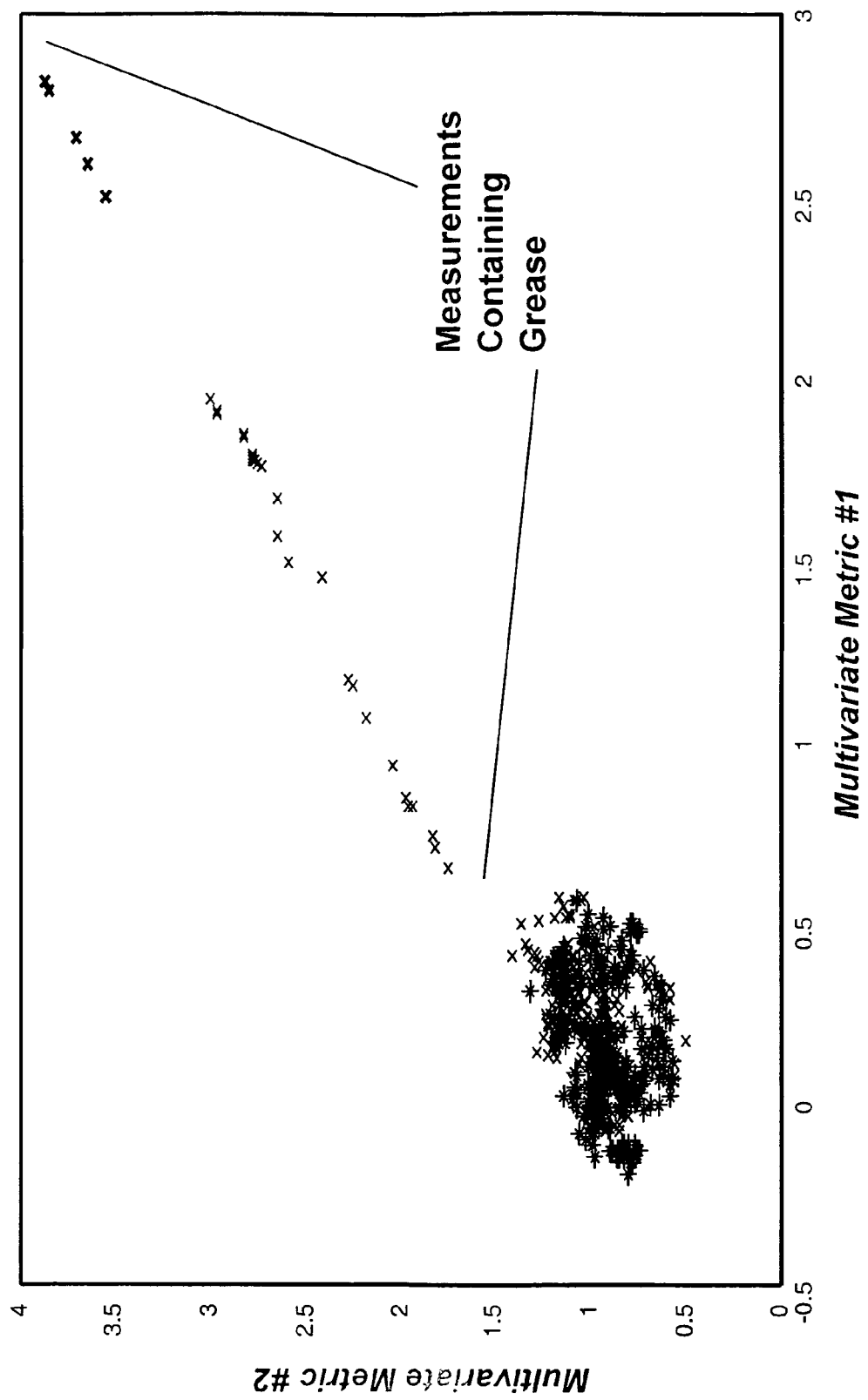
FIG. 17 shows example outlier metric values from noninvasive measurements.

The second method for mitigating the presence of topical interferents is to determine if one or more interferents is present on the sampling site. The multivariate calibration models used in the calibration subsystem offer inherent outlier metrics that yield important information regarding the presence of un-modeled interferents (topical or otherwise). As a result, they provide insight into the trustworthiness of the attribute measurement. FIG. 17 shows example outlier metric values from noninvasive measurements. All of the large metric values (clearly separated from the majority of the points)

correspond to measurements where grease had been intentionally applied to the subject's sampling site. These metrics do not specifically identify the cause of the outlier, but they do indicate that the associated attribute measurement is suspect. An inflated outlier metric value (a value beyond a fixed threshold, for example) could be used to trigger a fixed response such as a repeat of the measurement, application of an alternative calibration model, or a sampling site cleaning procedure. This is represented in FIG. 16 as the "Spectral Check OK" decision point.

The final topical interferent mitigation method involves adapting the calibration model to include the spectral signature of the topical interferent. The adapted calibration model can either be created on demand or selected from an existing library of calibration models. Each calibration in the library would be targeted at mitigating a different interferent or class of interferents such as oils. In some embodiments, the appropriate calibration model would be chosen based on the portion of an acquired spectrum that is unexplained by the original calibration model. This portion of the spectrum is referred to as the calibration model residual. Because each topical interferent or class of interferents has a unique Raman spectrum, the calibration model residual can be used to identify the topical interferent.

The model residual or the pure spectrum (obtained from a stored library) of the interferents can then be incorporated into the spectra used to form the calibration. The multivariate calibration is then reformed with the new spectra such that the portion of the attribute signal that is orthogonal to the interferent can be determined. The new calibration model is then used to measure the attribute of interest and thereby reduce the effects of the topical interferent on attribute measurement accuracy. The resulting model will reduce the effect of the interferent on the alcohol measurement at the expense of measurement precision when no interferents are present. This process is referred to as calibration immunization. It should be noted that, due to the impact of the immunization process on measurement precision, it is desirable to identify possible interferents for each measurement and immunize specifically against them rather than attempt to develop a calibration that is immunized against all possible interferents.

Raman Spectra of Tissue as a Biometric Signal

Figure 18:
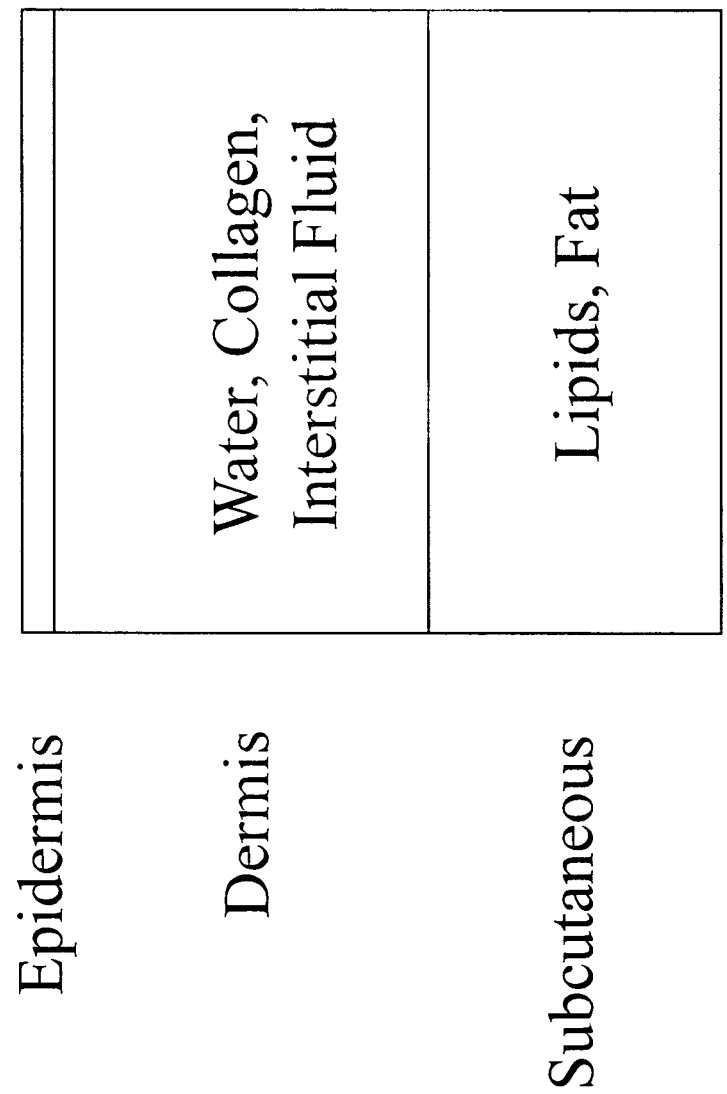
FIG. 18 is a diagram depicting the layered structure of skin tissue.

Human skin (FIG. 18) is comprised of epidermal, dermal, and subcutaneous layers, each of which has different physiological and chemical characteristics that influence their relative utility for alcohol measurements. The epidermis contains very little extracellular fluid, and therefore contains minimal information about hydrophilic analytes such as alcohol. The subcutaneous layer is largely comprised of lipids that have low water (and alcohol) solubility which make it poorly suited to alcohol measurements. However, the dermal layer has high water content (generally around 65%) and an extensive capillary bed conducive to the transport of alcohol, which makes it a useful layer of skin tissue for alcohol (or any analyte with high water solubility) measurements.

The layered structure of the tissue provides a wealth of spectroscopic information that can be used to discriminate between people. This biometric signal is a function of many skin properties such as the relative thicknesses of the tissue layers, their scattering coefficients, and the analyte concentrations within each layer. For example, the subcutaneous layer is largely comprised of lipids that are typically absent in other tissue layers. In contrast, the dermal layer is composed primarily of water and collagen. As a result, the spectroscopic measurement contains the relative signal contributions of these analytes and therefore provides insight into both the chemical composition and structure of the tissue. Because different people have different tissue properties (dermal hydration, collagen densities, tissue layer thicknesses), the spectroscopic measurement simultaneously captures both analyte signals (e.g. alcohol signal) and the inter-subject differences that collectively form the biometric signal.

Figure 19:
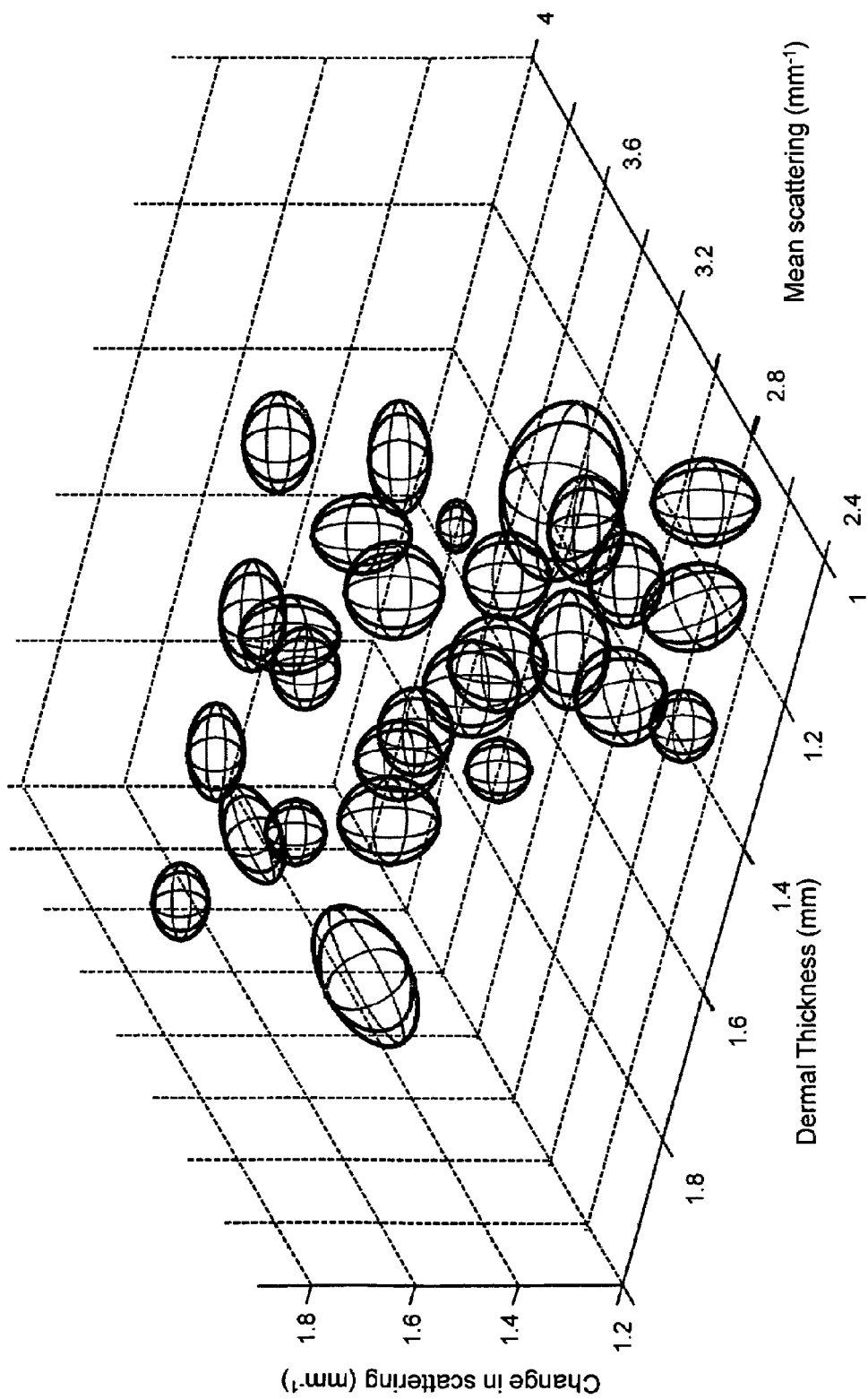
FIG. 19 shows an example ergonomic apparatus located on the measurement device.

FIG. 19 is a visual presentation of the inter-subject resolving power of the measurement using 3 extracted properties. Each ellipsoid in FIG. 19 encompasses the properties extracted from multiple measurements (typically 10-15) obtained from a single subject. Even with only three properties, the measurements acquired from each subject reside in a distinct region of the 3-dimensional space. This example can be extended to include additional properties and thereby further improve the discriminatory power of the biometric signal. The extracted properties can be representative of physical variables (e.g. dermal thickness or scattering coefficient) or mathematically derived from measurements of a subject (e.g. factors from a principal components analysis, PCA).

Biometric identification describes the process of using one or more physical or behavioral features to identify a person or other biological entity. There are two common biometric modes: identification and verification. Biometric identification attempts to answer the question of, "do I know you?" The biometric measurement device collects a set of biometric data from a target individual. From this information alone it assesses whether the person was previously enrolled in the biometric system. Systems that perform the biometric identification task, such as the FBI's Automatic Fingerprint Identification System (AFIS), are generally very expensive (several million dollars or more) and require many minutes to detect a match between an unknown sample and a large database containing hundreds of thousands or millions of entries. In biometric verification the relevant question is, "are you who you say you are?" This mode is used in cases where an individual makes a claim of identity using a code, magnetic card, or other means, and the device uses the biometric data to confirm the identity of the person by comparing the target biometric data with the enrolled data that corresponds with the purported identity. The present apparatus and methods for monitoring the presence or concentration of alcohol or substances of abuse in controlled environments can use either biometric mode.

There also exists at least one variant between these two modes that is also suitable for use in the present invention. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used in methods where the tested individual must be both part of the authorized group and sober but their specific identity is not required. The term "identity characteristic" includes all of the above modes, variants, and combinations or variations thereof.

There are three major data elements associated with a biometric measurement: calibration, enrollment, and target spectral data. The calibration data are used to establish spectral features that are important for biometric determinations. This set of data consists of series of spectroscopic tissue measurements that are collected from an individual or individuals of known identity. These data can be collected over a period of time and a set of conditions such that multiple spectra are collected on each individual while they span nearly the full range of physiological states that a person is expected to go through. In addition, the instrument or instruments used for spectral collection generally should also span the full range of instrumental and environmental effects that it or sister instruments are likely to see in actual use. These calibration data are then analyzed in such a way as to establish spectral wavelengths or "factors" (i.e. linear combinations of wavelengths or spectral shapes) that are sensitive to between-person spectral differences while minimizing sensitivity to within-person, instrumental (both within- and between-instruments), and environmental effects. These wavelengths or factors are then used subsequently to perform the biometric determination tasks.

The second major set of spectral data used for biometric determinations is the enrollment spectral data. The purpose of the enrollment spectra for a given subject or individual is to generate a "representation" of that subject's unique spectroscopic characteristics. Enrollment spectra are collected from individuals who are authorized or otherwise required to be recognized by the biometric system. Each enrollment spectrum can be collected over a period of seconds or minutes. Two or more enrollment measurements can be collected from the individual to ensure similarity between the measurements and rule out one or more measurements if artifacts are detected. If one or more measurements are discarded, additional enrollment spectra can be collected. The enrollment measurements for a given subject can be averaged together, otherwise combined, or stored separately. In any case, the data are stored in an enrollment database. In some cases, each set of enrollment data are linked with an identifier (e.g. a password or key code) for the persons on whom the spectra were measured. In the case of an identification task, the identifier can be used for record keeping purposes of who accessed the biometric system at which times. For a verification task, the identifier is used to extract the proper set of enrollment data against which verification is performed.

The third and final major set of data used for the biometric system is the spectral data collected when a person attempts to use the biometric system for identification or verification. These data are referred to as target spectra. They are compared to the measurements stored in the enrollment database (or subset of the database in the case of identity verification) using the classification wavelengths or factors obtained from the calibration set. In the case of biometric identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of biometric verification, the target spectrum is accompanied by an asserted identity that is collected using a magnetic card, a typed user name or identifier, a transponder, a signal from another biometric system, or other means. The asserted identity is then used to retrieve the corresponding set of spectral data from the enrollment database, against which the biometric similarity determination is made and the identity verified or denied. If the similarity is inadequate, then the biometric determination is cancelled and a new target measurement may be attempted.

In one method of verification, principle component analysis is applied to the calibration data to generate spectral factors. These factors are then applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in an example method for biometric identification, the Mahalanobis distance and spectral residual magnitude are calculated for the target spectrum relative each of the database spectra. The identify of the person providing the test spectrum is established as the person or persons associated with the database measurement that gave the smallest Mahalanobis distance and spectral residual magnitude that is less than a predetermined threshold set for each.

In an example method, the identification or verification task is implemented when a person seeks to perform an operation for which there are a limited number of people authorized (e.g., perform a spectroscopic measurement, achieve entry at a controlled facility, pass through an immigration checkpoint, etc.). The person's spectral data is used for identification or verification of the person's identity. In this example method, the person initially enrolls in the system by collecting one or more representative tissue spectra. If two or more spectra are collected during the enrollment, then these spectra be checked for consistency and recorded only if they are sufficiently similar, limiting the possibility of a sample artifact corrupting the enrollment data. For a verification implementation, an identifier such as a PIN code, magnetic card number, username, badge, voice pattern, other biometric, or some other identifier can also be collected and associated with the confirmed enrollment spectrum or spectra.

In subsequent use, biometric identification would take place by collecting a spectrum from a person attempting to gain authorization. This spectrum would then be compared to the spectra in the enrolled authorization database and an identification made if the match to an authorized database entry was better than a predetermined threshold. The verification task is similar, but would require that the person present the identifier in addition to a collected spectrum. The identifier would then be used to select a particular enrollment database spectrum and authorization would be granted if the current spectrum was sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

Another aspect of the present invention is the ability to update an individual's enrollment spectrum upon successful biometric authorization. In other words, once a given individual's identity has been verified or determined, the new measurement can be used to update the enrollment spectrum stored on the device, thereby allowing the enrollment to be robust against spectral changes caused by physiological drift of the individual. The enrollment updating can be accomplished by a variety of means including, but not limited to, direct replacement, averaging, weighted averaging, or other mathematical combinations. Those skilled in the art will recognize a variety of techniques for implementing embodiments of enrollment updating.

The biometric measurement, regardless of mode, can be performed in a variety of ways including linear discriminant analysis, quadratic discriminant analysis, K-nearest neighbors, neural networks, and other multivariate analysis techniques or classification techniques. Some of these methods rely upon establishing the underlying spectral shapes (factors, loading vectors, eigenvectors, latent variables, etc.) in the intra-person calibration database, and then using standard outlier methodologies (spectral F ratios, Mahalanobis distances, Euclidean distances, etc.) to determine the consistency of an incoming measurement with the enrollment database. The underlying spectral shapes can be generated by multiple means as disclosed herein.

First, the underlying spectral shapes can be generated based upon simple spectral decompositions (Eigen analysis, Fourier analysis, etc.) of the calibration data. The second method of generating underlying spectral shapes relates to the development of a generic model as described in U.S. Pat. No. 6,157,041, entitled "Methods and Apparatus for Tailoring Spectroscopic Calibration Models," which is incorporated by reference. In this application, the underlying spectral shapes are generated through a calibration procedure performed on intra-person spectral features. The underlying spectral shapes can be generated by the development of a calibration based upon simulated constituent variation. The simulated constituent variation can model the variation introduced by real physiological or environmental or instrumental variation or can be simply be an artificial spectroscopic variation. It is recognized that other means of determining underlying shapes would be applicable to the identification and verification methods of the present invention. These methods can be used either in conjunction with, or in lieu of the aforementioned techniques.

FURTHER EXAMPLES

Methods according to the present invention can comprise:

Example Method 1

A method for the non-invasive determination of an attribute of a human tissue of an individual by Raman spectroscopy, comprising:
a. illuminating a portion the tissue with excitation light,
b. collecting light from the tissue, and
c. determining the attribute from the detected light and a model relating Raman scattering and the attribute.

Example Method 2

The method of Example Method 1, further comprising determining at least one additional attribute from the detected light using a model relating Raman scattering to the at least one additional attribute.

Example Method 3

The method of Example Method 1, further comprising combining biologic information of the individual with the model to determine the attribute. Example Method 4. The method of Example Method 1, wherein the attribute comprises analyte presence, analyte concentration, rate or direction of change of analyte concentration, or combinations and subsets thereof.

Example Method 5

The method of Example Method 4, wherein the analyte comprises alcohol.

Example Method 6

The method of Example Method 4, wherein the analyte comprises a substance of abuse.

Example Method 7

The method of Example Method 4, wherein the analyte comprises an alcohol byproduct.

Example Method 8

The method of Example Method 1, wherein the tissue comprises blood. Example Method 9. The method of Example Method 1, wherein the tissue comprises skin of the forearm, finger, palm, hand, or wrist.

Example Method 10

The method of Example Method 1, wherein the attribute comprises biometric data.

Example Method 11

The method of Example Method 10, further comprising determining the identity of the individual from the biometric data.

Example Method 12

The method of Example Method 11, wherein determining the identity of the individual comprises determining whether the individual is among an enrolled set of individuals.

Example Method 13

The method of Example Method 12, wherein determining the identity of the individual comprises comparing a Raman spectrum of the detected light for the individual to enrollment spectra of the enrolled set of individuals.

Example Method 14

The method of Example Method 10, further comprising verifying the identity of the individual from the biometric data.

Example Method 15

The method of Example Method 14, wherein the identity verifying step comprises comparing a Raman spectrum of the detected light for the individual to an enrollment spectrum for the individual.

Example Method 16

The method of Example Method 1, wherein the illuminating step comprises illuminating the tissue with excitation light delivered from an optical input and the detecting step comprises collecting the emitted light with an optical output and the method further comprises orienting the optical input and the optical output to target a compartment of the tissue pertinent to the attribute.

Example Method 17

The method of Example Method 1, wherein the determining step comprises spectrally separating the detected light to provide a measured Raman spectrum and the method further comprises correcting the measured Raman spectrum.

Example Method 18

The method of Example Method 16, wherein the correcting step comprises correcting the measured Raman spectrum for tissue scattering and absorption of the excitation light and the emitted light to provide an intrinsic tissue Raman emission.

Example Method 19

The method of Example Method 1, wherein a Raman spectrum from an individual is adjusted by an enrollment spectrum from the individual.

Example Method 20

The method of Example Method 19, wherein the enrollment spectrum of an individual is mathematically adjusted by a Raman spectrum upon successful identity determination or verification.

Example Method 21

The method of Example Method 1, wherein the determining step comprises collecting calibration or training data and establishing a mathematical relationship between the training data and the attribute represented in the training data.

Example Method 22

The method of Example Method 1, further comprising mitigating the presence of a topical interferent on the attribute determination.

Example Method 23

The method of Example Method 22, wherein the topical interferent mitigating step comprises removing the topical interferent from the tissue prior to the detecting step.

Example Method 24

The method of Example Method 22, wherein the topical interferent mitigating step comprises removing outlier measurements from the attribute determining step.

Example Method 25

The method of Example Method 22, wherein the topical interferent mitigating step comprises adapting the model in the attribute determining step to include a spectral signature of the topical interferent.

Apparatuses according to the present invention can comprise:

Example Apparatus 1

An apparatus for the non-invasive determination of an attribute of a human tissue of an individual by Raman spectroscopy, comprising:
a. an illumination subsystem for generating excitation light,
b. a sampling subsystem for delivering the excitation light to a portion of the tissue and detecting light from the tissue,
c. a spectrometer subsystem for determining a Raman spectrum from the detected light
d. a computing subsystem for correcting the measured Raman spectrum, and
e. a calibration subsystem for determining the relationship between the corrected Raman spectrum and the attribute.

Example Apparatus 2

The apparatus of Example Apparatus 1, wherein the illumination subsystem comprises a light source comprising a continuous wave diode laser; a pulsed, modulated or mode-locked laser; a solid-state laser; an organic light emitting diode; a solid state light emitting diode; a gas laser; or a broad-band light source with a line filter.

Example Apparatus 3

The apparatus of Example Apparatus 1, wherein the illumination system comprises an optical diffuser or scrambler to provide reproducible and uniform radiance at the input of the sampling subsystem.

Example Apparatus 4

The apparatus of Example Apparatus 23, wherein the optical diffuser or scrambler comprises a ground glass plate, a reflective integrating chamber, a diffuse integrating chamber, a homogenizer, or a light pipe.

Example Apparatus 5

The apparatus of Example Apparatus 1, wherein the sampling subsystem comprises:
a. an optical input to receive the excitation light from the illumination subsystem,
b. a sampling surface that forms a tissue interface to illuminate the tissue with the excitation light delivered from the optical input, and
c. an optical output to collect the emitted light from the tissue and output the collected light to the spectrometer subsystem.

Example Apparatus 6

The apparatus of Example Apparatus 5, further comprising an ergonomic apparatus to hold the sampling surface and the position of the tissue at the interface.

Example Apparatus 7

The apparatus of Example Apparatus 5, further comprising a line filter between the optical input and the tissue to pass a narrow bandwidth of the excitation light from the illumination subsystem.

Example Apparatus 8

The apparatus of Example Apparatus 5, further comprising a light pipe or homogenizer between the optical output and the spectrometer subsystem.

Example Apparatus 9

The apparatus of Example Apparatus 5, further comprising a high pass filter between the sampling surface and the spectrometer subsystem.

Example Apparatus 10

The apparatus of Example Apparatus 5, wherein the optical input and the optical output comprise one or more channels, each channel comprising a specific orientation of the optical input and the optical output.

Example Apparatus 11

The apparatus of Example Apparatus 10, wherein the one or more channels are oriented to target a compartment of the tissue pertinent to the attribute.

Example Apparatus 12

The apparatus of Example Apparatus 5, wherein at least one of the optical input and the optical output comprises one or more optical fibers.

Example Apparatus 13

The apparatus of Example Apparatus 12, wherein the input and output optical fibers are arranged in concentric rings with a cylindrical gap therebetween.

Example Apparatus 14

The apparatus of Example Apparatus 12, wherein the input and output optical fibers are arranged in a linear geometry.

Example Apparatus 15

The apparatus of Example Apparatus 12, wherein the optical input and the optical output comprise the same optical fibers.

Example Apparatus 16

The apparatus of Example Apparatus 5, wherein at least one of the optical input and the optical output comprises a light pipe, lens, or mirror.

Example Apparatus 17

The apparatus of Example Apparatus 1, wherein the sampling subsystem further comprises a thermostat to maintain a constant temperature of the tissue.

Example Apparatus 18

The apparatus of Example Apparatus 1, wherein the sampling subsystem further comprises an index matching fluid between the sampling surface and the tissue.

Example Apparatus 19

The apparatus of Example Apparatus 1, wherein the spectrometer subsystem comprises a dispersive spectrometer.

Example Apparatus 20

The apparatus of Example Apparatus 1, wherein the spectrometer subsystem comprises an interferometric/modulating spectrometer.

Example Apparatus 21

The apparatus of Example Apparatus 20, wherein the interferometric/modulating spectrometer comprises a Fourier Transform spectrometer.

Example Apparatus 22

The apparatus of Example Apparatus 1, wherein the computer subsystem comprises means for correcting the measured spectrum for tissue scattering and absorption of the excitation light and the emitted light to provide an intrinsic tissue Raman emission.

Example Apparatus 23

The apparatus of Example Apparatus 1, wherein the computer subsystem comprises means for subtracting an enrollment spectrum for the individual from the measured Raman spectrum.

Example Apparatus 24

The apparatus of Example Apparatus 1, further comprising a biometric measurement device for collecting biometric data of the individual.

Example Apparatus 25

The apparatus of Example Apparatus 24, further comprising means for identifying the individual by comparing the biometric data of the individual with enrollment data for an enrolled set of individuals.

Example Apparatus 26

The apparatus of Example Apparatus 25, wherein the identifying means comprises comparing a Raman spectrum of the detected light for the individual to enrollment spectra of the enrolled set of individuals.

Example Apparatus 27

The apparatus of Example Apparatus 24, further comprising means for verifying the individual by comparing the biometric data of the individual with enrollment data for the individual.

Example Apparatus 28

The apparatus of Example Apparatus 27, wherein the verifying means comprises comparing a Raman spectrum of the detected light for the individual to an enrollment spectrum for the individual.

Example Apparatus 29

The apparatus of Example Apparatus 6 wherein the ergonomic apparatus mounts with the tissue of the individual.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What is claimed is:

1. A method for the non-invasive determination of an attribute of a human tissue of an individual by Raman spectroscopy using a single spectrometer, wherein the spectrometer comprises a detector configured to detect light incident thereon, the method comprising:
    (a) illuminating a portion the tissue with excitation light, where the tissue is not the eye;
    (b) collecting light from the tissue and generating a spectroscopic signal using the single spectrometer subsystem, wherein the spectroscopic signal includes information from at least one of: a steady state Raman measurement, a time-resolved Raman measurement, a spontaneous Raman measurement, a surface-enhanced Raman scattering (SERS) measurement, an anti-Stokes Raman scattering measurement, and a coherent anti-Stokes Raman spectroscopy (CARS) measurement, and wherein wavelength information obtained from a reference beam in connection with the spectroscopic signal is obtained with the detector, and wherein wavelength information obtained from the tissue in connection with the spectroscopic signal is obtained with the same detector; and (c) determining the attribute from the spectroscopic signal and a multivariate model relating spectroscopic signals from Raman scattering and the attribute.

2. The method of claim 1, further comprising determining at least one additional attribute from the spectroscopic signal using a model relating spectroscopic signals from Raman scattering to the at least one additional attribute.

3. The method of claim 1, further comprising combining biologic information of the individual with the model to determine the attribute.

4. The method of claim 1, wherein the attribute comprises analyte presence, analyte concentration, rate or direction of change of analyte concentration, or combinations and subsets thereof.

5. The method of claim 4, wherein the analyte comprises alcohol.

6. The method of claim 4, wherein the analyte comprises a substance of abuse.

7. The method of claim 4, wherein the analyte comprises an alcohol byproduct.

8. The method of claim 1, wherein the tissue comprises tissue containing a plurality of constituents that display Raman scattering at one or more wavelengths in common with the wavelengths at which the analyte exhibits electronic absorption.

9. The method of claim 1, wherein the tissue comprises skin of the forearm, finger, palm, hand, or wrist.

10. The method of claim 1, wherein the attribute comprises biometric data.

11. The method of claim 10, further comprising determining the identity of the individual from the biometric data.

12. The method of claim 11, wherein determining the identity of the individual comprises determining whether the individual is among an enrolled set of individuals.

13. The method of claim 12, wherein determining the identity of the individual comprises comparing a Raman spectrum of the detected light for the individual to enrollment spectra of the enrolled set of individuals.

14. The method of claim 10, further comprising verifying the identity of the individual from the biometric data.

15. The method of claim 14, wherein the identity verifying step comprises comparing a Raman spectrum of the detected light for the individual to an enrollment spectrum for the individual.

16. The method of claim 1, wherein the illuminating step comprises illuminating the tissue with excitation light delivered from an optical input and the detecting step comprises collecting the emitted light with an optical output and the method further comprises orienting the optical input and the optical output to target a compartment of the tissue pertinent to the attribute.

17. The method of claim 1, wherein the determining step comprises spectrally separating the detected light to provide a measured Raman spectrum and the method further comprises correcting the measured Raman spectrum.

18. The method of claim 17, wherein the correcting step comprises correcting the measured Raman spectrum for tissue scattering and absorption of the excitation light and the emitted light to provide an intrinsic tissue Raman emission.

19. The method of claim 1, wherein a Raman spectrum from an individual is adjusted by an enrollment spectrum from the individual.

20. The method of claim 19, wherein the enrollment spectrum of an individual is mathematically adjusted by a Raman spectrum upon successful identity determination or verification.

21. The method of claim 1, wherein the determining step comprises collecting calibration or training data and establishing a mathematical relationship between the training data and the attribute represented in the training data.

22. The method of claim 1, further comprising mitigating the presence of a topical interferent on the attribute determination.

23. The method of claim 22, wherein the topical interferent mitigating step comprises removing the topical interferent from the tissue prior to the detecting step.

24. The method of claim 22, wherein the topical interferent mitigating step comprises removing outlier measurements from the attribute determining step.

25. The method of claim 22, wherein the topical interferent mitigating step comprises adapting the model in the attribute determining step to include a spectral signature of the topical interferent.

* * * * *